United States Patent
Smith et al.

(10) Patent No.: US 7,998,681 B2
(45) Date of Patent: *Aug. 16, 2011

(54) DIAGNOSIS AND THERAPY OF ANTIBODY-MEDIATED INFLAMMATORY AUTO-IMMUNE DISORDERS

(75) Inventors: Terry J. Smith, Manhattan Beach, CA (US); William W. Cruikshank, Westford, MA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 923 days.

This patent is subject to a terminal disclaimer.

(21) Appl. No.: 10/038,509

(22) Filed: Jan. 3, 2002

(65) Prior Publication Data

US 2003/0096317 A1 May 22, 2003

Related U.S. Application Data

(63) Continuation-in-part of application No. 10/046,651, filed on Oct. 19, 2001, now Pat. No. 6,936,426, which is a continuation of application No. 09/684,601, filed on Oct. 6, 2000, now abandoned.

(51) Int. Cl.
    G01N 33/53   (2006.01)
    G01N 33/00   (2006.01)
    C12N 5/071   (2010.01)
(52) U.S. Cl. ............ 435/7.1; 435/7.92; 435/372.3
(58) Field of Classification Search ............ None
    See application file for complete search history.

(56) References Cited

U.S. PATENT DOCUMENTS

| | | | | |
|---|---|---|---|---|
| 5,766,866 | A | * | 6/1998 | Center et al. ......... 435/7.24 |
| 6,159,711 | A | | 12/2000 | Proudfoot et al. ...... 435/69.5 |
| 6,936,426 | B2 | * | 8/2005 | Smith et al. .......... 435/7.1 |

FOREIGN PATENT DOCUMENTS

WO    WO 96/17935    6/1996

OTHER PUBLICATIONS

Pritchard et al. 'Synovial Fibroblasts from Patients with Rheumatoid Arthritis, Like Fibroblasts from Graves' Disease, Express High Levels of IL-16 When Trested with Igs against Insulin-Like Growth Factor-1 Receptor.' J. Immunol. 173:3564-3569, 2004.*
Woodland et al. 'Heterogeneity of CD4+ and CD8+ T cells.' Curr. Opin. Immunol. 15:336-342, 2003.*
Kendall Taylor et al. 'IGF-I levels in culture supernatants of extraocular myoblasts rise in response to graves IgG.' J. Endocrinol. 124(Suppl) 1990.*
Weightman et al. 'IgG fractions from patients with Graves disease target the IGF-I receptor.' J. Endocrinol. 137(Suppl), 1993.*
Blaschke et al. 'Expression of the CD4+ Cell-specific chemoattractant interleukin-16 in mycosis fungoides.' J. Invest. Dermatol. 113:658-663, 1999.*

Schroder et al. 'Role of eosinophil-chemotactic C-C chemokines in cutaneous inflammation.' J. Leukoc. Biol. 59:1-5, 1996.*
Fukuoka et al. 'Regulation of RANTES and IL-8 production in normal human dermal fibroblasts by active vitamin D3 (tacalcitol).' Brit. J. of Pharmacol. 2124:1433-1438, 1998.*
Noso et al. 'Identification of an N-terminally truncated form of the chemokine RANTES and Granulocyte-Macrophage Colony-Stimulating Factor as Major eosinophil attractants released by cytokine-stimulated dermal fibroblasts.' J. Immunol. 156:1946-1953, 1996.*
Cai et al., "The intracellular signaling pathways involved in MCP-1-stimulated T cell migration across microvascular endothelium," *Cellular Immunology* 167(2):269-275 (1996).
Denko et al., "Growth factors, insulin-like growth factor-1 and growth hormone, in synovial fluid and serum of patients with rheumatic disorders," *Osteoarthritis and Cartilage*, 4(4):245-249 (1996).
Franz et al., "Interleukin-16, produced by synovial fibroblasts, mediates chemoattraction for CD4+ T lymphocytes in rheumatoid arthritis," *Eur. J. Immunol.* 28(9):2661-2671 (1998).
Mira et al., "A role for chemokine receptor transactivation in growth factor signaling," *EMBO Reports*, 21(21):151-156 (2001).
Perros et al., "Thyroid-associated opthalmopathy: pathogenesis and clinical management," *Balliere's Clinical Endocrinology and Metabolism*, 9(1):115-135 (1995).
Poggi et al., "Phenotypic and functional analysis of CD4+ NKRP1A+ human T lymphocytes. Direct evidence that the NKRP1A molecule is involved in transendothelial migration," *Eur. J. Immunol.* 27(9):2345-2350 (1997).
Schrieber, "Immunomodulators," *Agents and Actions Supplements*, 24:254-264 (1988).
Nicoll et al., "Identification of Domains in IL-16 Critical for Biological Activity," *Journal of Immunology* 163:1827-1832 (1999).
Simchen et al., "Expression and Regulation of Regulated on Activation, Normal T Cells Expressed and Secreted in Thyroid Tissue of Patients with Graves' Disease and Thyroid Autonomy and in Thyroid-Derived Cell Population," *Journal of Clinical Endocrinology and Metabolism*, 85:4758-4764 (2000).
Weightman et al., "Autoantibodies to IGF-1 Binding Sites in Thyroid Associated Ophthalmopathy," *Autoimmunity* 16:251-257 (1993).
Bell et al., "Functional TSH receptor in human abdominal preadipocytes and orbital fibroblasts," *Am. J. Physiol. Cell Physiol.* 279:C335-C340 (2000).
Brennan et al., "p70$^{06k}$ Integrates Phosphatidylinositol 3-Kinase and Rapamycin-Regulated Signals for E2F Regulation in T Lymphocytes," *Mol. Cell Biol.* 19(7):4729-4738 (1999).
Wong et al., "RANTES Activates Jak2 and Jak3 to Regulate Engagement of Multiple Signaling Pathways in T Cells," *J. Biol. Chem.* 276:11427-11431 (2001).

(Continued)

*Primary Examiner* — Nora Rooney
(74) *Attorney, Agent, or Firm* — Jones Day

(57) ABSTRACT

The present invention describes diagnosis and treatment of antibody-mediated inflammatory auto-immune diseases. The biochemical mechanisms underlying such disorders are described as characteristic molecular markers and antibody-mediated ligand-receptor interactions. Specifically, the activation of T-cells by disease specific IgG binding to the IGF-1 receptor is shown to underlie thyroid associated ophthalmopathy associated with Graves' disease and rheumatoid arthritis. Diagnostics for detection of disease are provided, as are therapeutics based on the determination of the mechanisms underlying a particular pathology.

6 Claims, 16 Drawing Sheets

OTHER PUBLICATIONS

Laugwitz et al., "The human thyrotropin receptor: A heptahelical receptor capable of stimulating members of all four G protein families," *Proc. Natl. Acad. Sci.* USA 93:116-120 (1996).

Lim et al., "Human Eosinophils Elaborate the Lymphocyte Chemoattractants," *J. Immunol.* 156:2566-2570 (1996).

Matsumoto et al., "Arthritis Provoked by Linked T and B Cell Recognition of a Glycolytic Enzyme," *Science* 286:1732-1735 (1999).

Popovich et al., "Concept of Autoimmunity Following Spinal Cord Injury: Possible Roles for T Lymphocytes in the Traumatized Central Nervous System," *J. Neurosci. Res.* 45:349-363 (1996).

Pritchard et al., "Igs from Patients with Graves' Disease Induce the Expression of T Cell Chemoattractants in Their Fibroblasts," *J. Immunol.* 168:942-950 (2002).

Rotella et al., "Ability of Monoclonal Antibodies to the Thyrotropin Receptor to Increase Collagen Synthesis in Human Fibroblasts: An Assay which Appears to Measure Exophthalmogenic Immunoglobulins in Graves' Sera," *J. Clin. Endocrinol. Metabol.* 62:357-367 (1986).

Sciaky et al., "Cultured Human Fibroblasts Express Constitutive IL-16 mRNA: Cyokine Induction of Active IL-16 Protein Synthesis Through a Caspase-3-Dependent Mechanism," *J. Immunol.* 164:3806-3814 (2000).

Smith et al., "Fibroblasts as Sentinel Cells," *Am. J. Pathol.* 151:317-322 (1997).

Ullrich et al., "Insulin-like growth factor I receptor primary structure: comparison with insulin receptor suggests structural determinants that define functional specificity," *EMBO J.* 5(10):2503-2512 (1986).

* cited by examiner

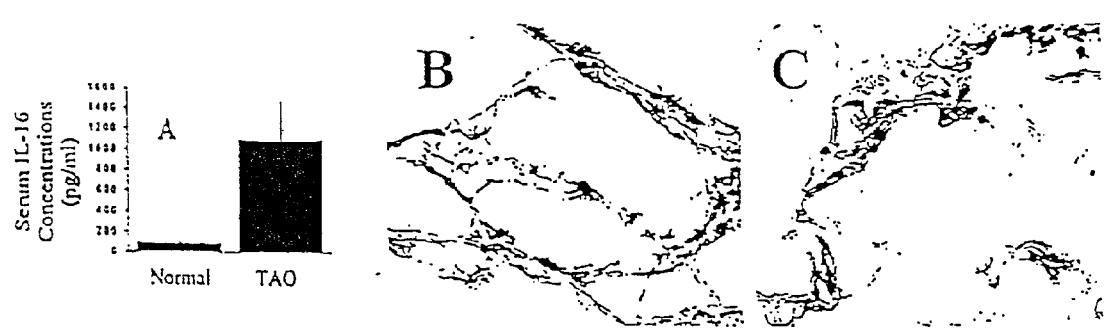
FIGURE 3 A, B & C

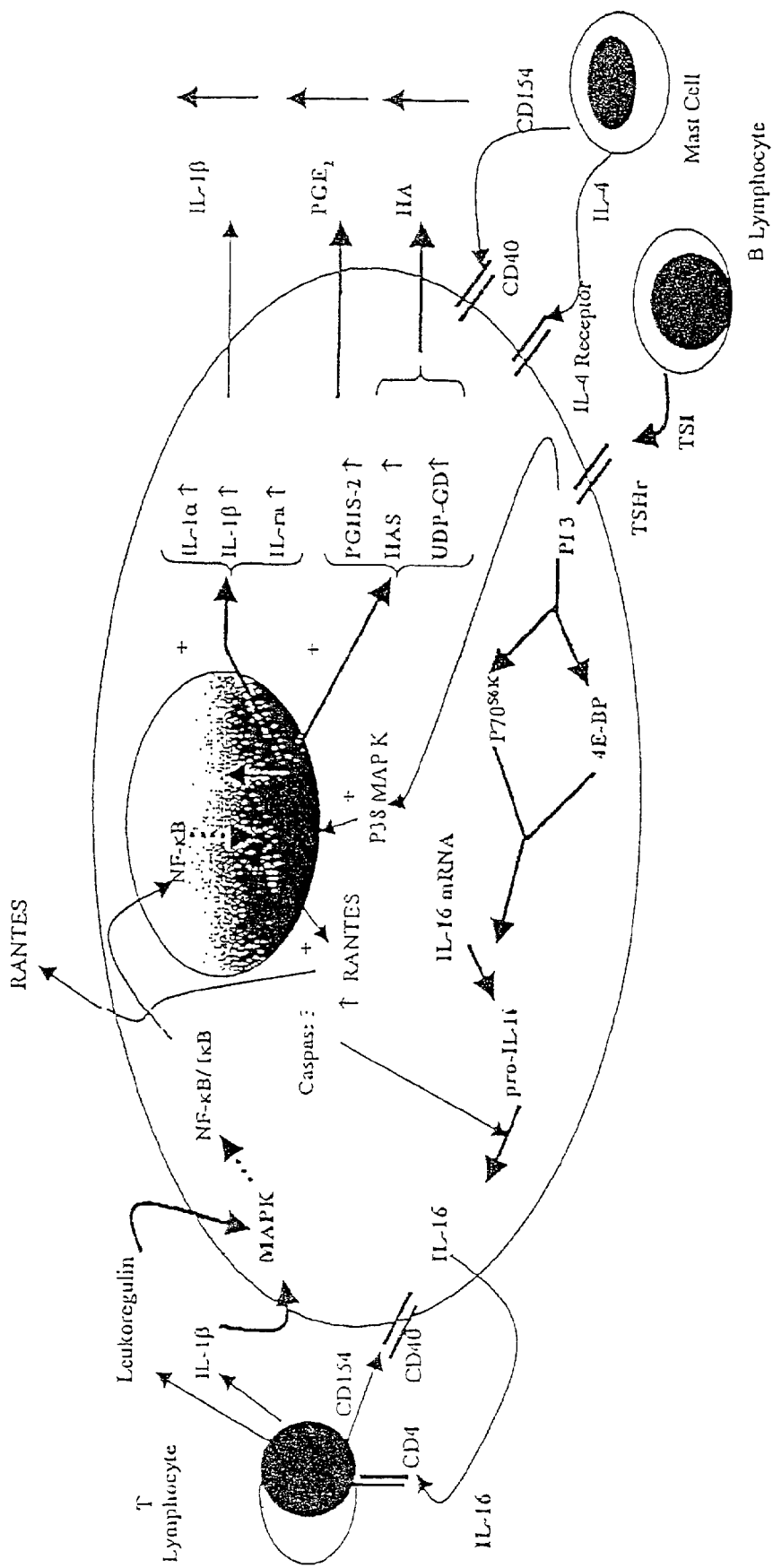
FIGURE 5 (overview)

DIAGNOSIS AND THERAPY OF ANTIBODY-MEDIATED INFLAMMATORY AUTO-IMMUNE DISORDERS

This application is a continuation-in-part of U.S. application Ser. No. 10/046,651 filed on Oct. 19, 2001, now U.S. Pat. No. 6,936,426, which is a continuation of U.S. application Ser. No. 09/684,601, filed on Oct. 6, 2000 now abandoned.

FIELD OF THE INVENTION

This invention was made in part from government support under Grant Nos. RO1 EY 8976 AND RO1 EY 11708; HL 32802 from the National Institute of Health (NIH) of the United States. The U.S. Government may have certain rights in this invention.

The present invention is therapeutics and diagnostics of antibody-mediated inflammatory auto-immune diseases and other pathologies having common underlying mechanisms. Examples are the connective tissue pathologies associated with Graves' disease, also known as Thyroid-Associated Ophthalmopathy (TAO), rheumatoid arthritis (RA), systemic lupus erythematosus (SLE), ulcerative colitis, scleroderma, Type II diabetes, and Crohn's disease. The therapeutic component of this invention comprises administering to a patient suffering from an antibody-mediated inflammatory auto-immune disorder a compound selected to interrupt a fundamental mechanism or pathway necessary to the manifestation of the disorder, including compounds that reduce the unique susceptibility of orbital fibroblasts to pro-inflammatory cytokines, inhibitors of activated T-lymphocyte-based infiltration of orbital connective tissue and resident fibroblasts, agents to reduce or attenuate the signaling exhibited in the FRAP/mTOR/$p70^{s6k}$ pathway, compounds to reduce the activation of the PI3 kinase pathway, compounds to attenuate the binding or function of the IGF-1 receptor, and compounds to blocking disease specific IgG from binding the IGF-1 receptor, including specifically blocking Graves' IgG and rheumatoid arthritis IgG from binding orbital fibroblast and synovial fibroblasts, respectively.

In the specific application of Graves' disease or RA, the invention provides compounds to attenuate the activity of receptors underlying the disease including antagonists, inverse-agonists, and anti-agonists of the IGF-1 receptor, as well as inhibitors of the expression of Interleukin 16 (IL-16) and/or a RANTES to decrease the proliferation of CD4-bearing lymphocytes at the site of the disease. An especially preferred inhibitor of IL-16 expression for use in the therapeutic methods of the present invention is rapamycin, and an especially preferred RANTES inhibitor for use in the present invention is compound SB203580. The present invention also includes diagnostic tests and methods to determine the susceptibility or presence of disease characterized by an antibody-mediated inflammatory auto-immune disorder, including the detection of specific receptors or other molecular markers as indicators of disease, the detection of the function or activation of the receptor or marker in a particular patient, and the existence of specific markers as auto-antigens. In the specific embodiment of Graves' disease and RA, the invention includes a method to identify the presence of disease specific auto-immune-associated antibodies via the reaction with specified cell types by reacting a patient sample in an assay and measuring a compound indicative of the presence of disease, including measuring the levels of IL-16 and/or RANTES in a biological sample, detecting specific auto-immune antibodies or cell receptor types in the sample obtained from the patient, detecting phenotype fibroblast subsets, and detecting the presence of specific receptors as auto-antigens. The diagnostic embodiment of the invention also includes identifying in a patient sample the orbital fibroblasts that exhibit differential phenotypes associated with adipogenesis and the correlation of the presence of these specific fibroblasts with in vivo differentiation into adipocytes. Application of the diagnostic embodiments of the invention may also instruct the clinician as to therapeutic treatments including the administration of compounds described herein, as well as traditional surgical techniques used in alleviating eye disorders associated with Graves' disease.

BACKGROUND OF THE INVENTION

Graves' disease is an example of an antibody-mediated inflammatory auto-immune disorder that is clinically manifested as an expansion of the orbital contents and associated severe inflammation of the connective tissue and extra-ocular muscles. Graves' disease is caused by a hyper-functioning, diffuse, hyperplastic thyroid goiter, often accompanied by infiltrative ophthalmopathy and infiltrative dermopathy. Graves' disease is present in 1.5% to 2% of women in the United States, but is only one-tenth as common among men, and is rare in children. Familial predisposition has been noted frequently. A well-defined relationship also exists between Graves' disease and other auto-immune diseases, such as pernicious anemia and rheumatoid arthritis, which occur with greater than normal frequency in patients with Graves' disease. With TAO, characteristic tissue remodeling occurs in the orbital area, including lymphocyte infiltration, hyaluronan accumulation, and inflammation.

Like many auto-immune disorders, Graves' disease and rheumatoid arthritis are difficult to manage clinically because currently available treatments are either ineffective or have significant side effects, due largely to the lack of specificity of the treatment. The absence of any satisfactory therapies is also directly attributable to the current poor understanding of the fundamental biochemical pathways and mechanisms underlying the disease process. Left untreated, subtle changes in cell signalling and molecular immunological mechanisms associated with such disorders result in profound physical defects. Rheumatoid arthritis is painful and the chronic condition can be almost totally debilitating. In TAO, the orbital space is constrained by bone and thus small increases in the volume of soft tissue will cause the anterior displacement of the eye (proptosis). Proptosis occurs in TAO, where the endomysial connective tissue and fat/connective tissue in the orbit are infiltrated with immunocompetent cells such as lymphocytes, macrophages and mast cells. (Smith, T. J., Bahn, R. S. and Gorman, C. A.: Connective tissue, glycosaminoglycans and diseases of the thyroid. *Endocrine Rev.* 10:366-391, 1989). The inflammatory reaction is sometimes intense. A major component of the tissue remodeling seen in the orbit in TAO relates to the accumulation of the non-sulfated glycosaminoglycan, hyaluronan. Hyaluronan possesses a set of rheological properties that render the molecule extraordinarily hydrophilic (Smith, T. J., Bahn, R. S. and Gorman, C. A.: Connective tissue, glycosaminoglycans and diseases of the thyroid. *Endocrine Rev.* 10:366-391, 1989). Thus, even a small increase in the hyaluronan content of a tissue could increase its volume dramatically. In the setting of the bony orbit, such an increase could yield catastrophic consequences to the integrity of soft tissue structures, innervation and vascularity.

Debate exists as to whether the primary focus of the pathogenic process in TAO is directed at the extraocular musculature or the connective/adipose tissue in the orbit. In many cases, enlargement of the extraocular musculature appears to be more dramatic than that of the fat pad (Smith, T. J., Bahn, R. S. and Gorman, C. A.: Connective tissue, glycosaminoglycans and diseases of the thyroid. *Endocrine Rev.* 10:366-391, 1989). The work of Smelser provided strong evidence that TAO is a fibroblast-related disease process (Smelser, G. K.: A comparative study of experimental and clinical exophthalmos. *Am. J. Ophthalmol.* 20:1189-1203, 1937). This group described the early disease as similar edematous changes occurring in both muscle and fat interstitium with minimal muscle degeneration. Subsequent light and transmission electron microscopic studies have confirmed the preservation of the motor elements of the muscles until very late in the disease process. The endomysium, rich with fibroblasts, accumulates hyaluronan, accounting for the volume changes observed in muscle.

Medical researchers are increasingly aware of the complexity with which connective tissue is regulated and of the diverse influences that elements of this tissue exert on neighboring cell types. Fibroblasts vary with regard to anatomic region of origin and synthesize numerous small regulatory molecules including cytokines and growth factors (Fries, K. M., Blieden, T., Looney, R. J., Sempowski, G. D., Slvera, M. R., Willis, R. A. and Phipps, R. P.: Evidence of fibroblast heterogeneity and the role of fibroblast populations in fibrosis. *Clin. Immunol. Immunopath.* 72:283-292, 1994). As described in detail herein, depending on the anatomic origin, fibroblasts are increasingly seen as gatekeeper cells for a variety of mechanisms, including specifically immunologic mechanisms that regulate cell signalling and cell activation. For example, the biosynthetic repertoires of orbital fibroblasts are vastly different from those found in other anatomic locations, their responses to hormones and growth factors and the extracellular matrix that they lay down are also different. (Smith, T. J., Aftab, A., Hogg, M. G. and Higgins, P. J.: Interferon-γ is an inducer of plasminogen activator inhibitor type 1 in human orbital fibroblasts. *Am. J. Physiol.* 263:C24-C29, 1992; Smith, T. J., Bahn, R. S., Gorman, C. A. and Cheavens, M.: Stimulation of glycosaminoglycan accumulation by interferon gamma in cultured human retroocular fibroblasts. *J. Clin. Endocrinol. Metab.* 72:1169-1171, 1991; Smith, T. J.: Dexamethasone regulation of glycosaminoglycan synthesis in cultured human skin fibroblasts: similar effects of glucocorticoid and thyroid hormones. *J. Clin. Invest.* 74:2157-2163, 1984; Smith, T. J., Bahn, R. S. and Gorman, C. A.: Hormonal regulation of hyaluronate synthesis in cultured human fibroblasts: evidence for differences between retroocular and dermal fibroblasts. *J. Clin. Endocrinol. Metab.* 69:1019-1023, 1989). Controversy also exists with regard to the phenotypes of lymphocytes predominating in the orbit of patients with TAO (McLachlan, S. M., Prummel, M. F. and Rapoport, B.: Cell-mediated or humoral immunity in Graves' ophthalmopathy? Profiles of T-cell cytokines amplified by polymerase chain reaction from orbital tissue. *J. Clin. Endocrinol. Metab.* 78:1070-1074, 1994; Jaume, J. C., Portolano, S., Prummel, M. F., McLachlan, S. M. and Rapoport, B., Molecular cloning and characterization of genes for antibodies generated by orbital tissue-infiltrating B-cells in Graves' ophthalmopathy. *J. Clin. Endocrinol. Metab.* 78:348-352, 1994; De Carli, M., D'Elios, M. M., Mariotti, S., Marcocci, C., Pinchera, A., Ricci, M., Romagnani, S. and Del Prete, G.: Cytolytic T cells with Th1-like cytokine profile predominate in retroorbital lymphocyte infiltrates of Graves' ophthalmopathy. *J. Clin. Endocrinol. Metab.* 77:1120-1124, 1993; Grubeck-Loebenstein, B., Trieb, K., Sztankay, A, Holter, W., Anderi, H. and Wick, G.: Retrobulbar T cells from patients with Graves' ophthalmopathy are CD8+ and specifically recognize autologous fibroblasts. *J. Clin. Invest.* 93:2738-2743, 1994).

The selective targeting of orbital connective tissue for activation in TAO associated with Graves' disease is not currently understood. A central question is why activated T and B lymphocytes are trafficked to the orbit. Interest has centered on the successful cloning of the thyrotropin or Thyroid Stimulating Hormone Receptor (TSHr) because patients with Graves' disease typically express high levels of antibodies against the TSHr receptor, which can be either stimulatory or inhibitory. Stimulatory anti-TSHr antibodies activate the receptor and yield increased cAMP levels, thyrocyte proliferation and thyroid hormone overproduction. Inhibitory TSHr antibodies attenuate thyroid gland activity. Studies examining the role of stimulatory and inhibitory anti-TSHr antibodies on the metabolism of cultured fibroblasts have been inconsistent. Rotella, C. M., Zonefrati, R., Toccafondi, R., Valente, W. A., and Kohn, L. D.: Ability of monoclonal antibodies to the thyrotropin receptor to increase collagen synthesis in human fibroblasts: an assay which appears to measure exophthalmogenic immunoglobulins in Graves' sera. *J. Clin. Endocrinol. Metab.* 62:357-367, 1986; Cheung, H. S., Nicoloff, J. T., Kamiel, M. B., Spolter, L. and Nimni, M. E.: Stimulation of fibroblasts biosynthetic activity by serum of patients with pretibal myxedema. *J. Invest. Dermatol.* 71:12-17, 1978.

TSHr is also implicated in the glandular component of Graves' disease by virtue of its activation by Thyroid Stimulating Immunoglobulin (TSI) resulting in hyperthyroidism. Recently, preliminary evidence was introduced suggesting that TSIs are heterogeneous (Drexhage, H. A.: Autoimmunity and thyroid growth. *Eur. J. Endocrinol.* 135:39-45, 1996). Moreover, different sub-classes of TSI might activate distinct signaling pathways in the thyroid. Until now, little insight existed concerning the actions of TSI on orbital fibroblasts. Thus, no connection had been identified between the presence of these immunoglobulins and the pathogenesis of TAO. A number of investigators have speculated that the TSHr might represent an auto-antigen relevant to TAO if anatomically restricted expression, shared by the orbit and the thyroid, could be established. Indeed, mRNA encoding the TSHr has been extracted from the orbits of patients with severe TAO as well as from normal orbital tissue (Feliciello, A., Porcellini, A., Ciullo, I., Bonavolonta, G., Avvedimento, E. V. and Fenzi, G., Expression of thyrotropin-receptor mRNA in healthy and Graves' disease retro-orbital tissue. Lancet 342:337-338, 1993). Moreover, TSHr mRNA has been detected in orbital fibroblasts by PCR amplification (Heufelder, A. E., Dutton, C. M., Sarkar, G., Donovan, K. A. and Bahn, R. S.: Detection of TSH receptor RNA in cultured fibroblasts from patients with Graves' ophthalmopathy and pretibial dermopathy. *Thyroid* 3:297-300, 1993).

Pro-inflammatory cytokines also have been implicated in the pathogenesis of TAO and orbital fibroblasts exhibit exaggerated responses to pro-inflammatory cytokines. A recent report suggested the presence of immunoreactive IL-1α in orbital connective tissue from patients with severe TAO (Heufelder, A. E. and Bahn, R. S.: Detection and localization of cytokine immunoreactivity in retro-ocular connective tissue in Graves' ophthalmopathy. *European J. Invest.* 23:10-17, 1993. 22. Dinarello, C. A.: Biologic basis for interleukin-1 in disease. *Blood* 87:2095-2147, 1996). IL-1 is a family of two cytokines designated IL-1α and IL-1β, each encoded by a separate gene but with substantial overlap in their biological actions (Dinarello, C. A.: Biologic basis for interleukin-1 in disease. *Blood* 87:2095-2147, 1996). IL-1α is primarily an intracellular molecule while IL-1β is exported to the outside of the cell expressing it. It would appear that these IL-1 proteins share common receptors. Bahn has also implicated leukoregulin, a T lymphocyte-derived cytokine, in the pathogenesis of TAO (Bahn, R. S.: Cytokines in thyroid eye disease. *Thyroid* 8:415-418, 1998). Leukoregulin is a 50 kDa cytokine that is expressed by activated T lymphocytes (Mauviel, A., Redini, F., Hartmann, D. J., Pujol, J.-P. and Evans, C. H.: Modulation of human dermal fibroblast extracellular matrix metabolism by the lymphokine leukoregulin. *J. Cell Biol.* 113:1455-1462, 1991) and acts through NF-KB to up-regulate inflammatory and extracellular matrix-encoding genes.

Thy-1 is a 25-35 kDa glycoprotein expressed by a wide variety of cells, although whose function as a receptor is uncertain. Thy-$1^+$ and Thy-$1^-$ are heterogeneously present in orbital fibroblasts. Approximately 50 to 60 percent of orbital fibroblasts in both TAO and normal orbital connective tissue express the Thy-1 receptor. Although the presence of the Thy-1 receptor is heterogeneous on orbital fibroblasts, Thy-$1^+$ and Thy-$1^-$ cells exhibit distinct and different phenotypes. Each phenotype may be characterized by expression of PGHS-2 upon exposure to IL-1 beta and the production of large amounts of $PGE_2$, although Thy-$1^+$ cells produce more $PGE_2$ than Thy-$1^-$ fibroblasts. Thy-$1^-$ cells are implicated in exaggerated foreign antigen presenting activity and have a greater potential for activating macrophages and lymphocytes. Therefore, while Thy-$1^+$ and Thy-$1^-$ fibroblasts exhibit different phenotypes and appear to participate differently in fundamental immune mechanisms and cell trafficking, the distinctions are not well-characterized.

IL-16 is a CD4-specific chemoattractant molecule not assigned to any chemokine family because the requisite cysteine signature residues for such designation are absent (Center, D. M., Kornfeld, H. and Cruikshank, W. W.: interleukin 16 and its function as a CD4 ligand. *Immunol. Today* 17:476-481, 1996). IL-16 was originally found to be expressed by activated CD8+ lymphocytes but subsequently has been found to be produced by mast cells, bronchial epithelium, and CD4+ lymphocytes. It has been cloned and found to be regulated by several factors in a cell-type-specific pattern. IL-16 is a CD4 ligand and when bound, leads to lymphocyte activation and IL-2 receptor up-regulation. It has been implicated in the pathogenesis of asthma and human auto-immune diseases such as rheumatoid arthritis and lupus. IL-16 was detected in synovial fluid and soft tissues of diseased joints (Franz, J. K., Kolb, S. A., Hummel, K. M., Lahrtz, F., Neidhart, M., Aicher, W. K., Pap, T., Gay, R. E., Fontana, A. and Gay, S.: Interleukin-16, produced by synovial fibroblasts, mediates chemoattraction of $CD4^+$ T lymphocytes in rheumatoid arthritis. *Eur. J. Immunol.* 28:2661-1998).

In addition to TAO, several other connective tissue disorders have been shown to have an antibody-mediated auto-immune component. For example, vitiligo, a depigmenting order of the skin, is caused by the destruction of melanocytes. Although the cause is still unknown, prominent theories explaining the mechanism of melanocyte destruction are auto-immune, autocytotoxicm and neural hypotheses. (S. O. Kovacs, *Vitiligo,* 38 J. Am. Acad. Dermatol. 647 (1998)). Pemphigus vulgaris is another antibody-mediated auto-immune disease affecting the skin. Antibodies against desmosomal adhesion molecules (Dsg3) are thought to be a major factor in the pathogenesis of the disease. Autoreactive T-cells, which recognize epitopes of Dsg3 in PV patients, preferentially produce TH2 cytokines such as IL-4 and IL-10. (M. Hertl and R. Riechers, Analysis of the T cells that are Potentially Involved in Autoantibody Production in Pemphigus Vulgaris, 26 J. Dermatol. 748 (1999).

Polyglandular auto-immune syndrome is used to describe the dysfunction of two or more endocrine glands occurring in association with circulating antibodies directed against the affected glands. The auto-immune nature of the syndrome is caused by the presence of lymphocytic infiltration of the affected gland, organ-specific autoantibodies, cellular immune defects, and an association with the immune response genes. The principal endocrine components include adrenal insufficiency, auto-immune thyroid disease, insulin-dependent diabetes mellitus, and premature gonadal failure. (M. Leshin, Polyglandular Autoimmune Syndromes, 290 Am. J. Med. Sci. 77 (1985); W. J. Riley, Autoimmune Polyglandular Syndromes, 38 Horm. Res. 9 (Suppl. 2) (1992)).

Type 1 diabetes, a disease affecting several million every year, is caused by auto-immune destruction of the B-cells in the pancreatic islets of Langerhans which produce insulin. Although it is required to be present, a certain genetic phenotype does not appear sufficient on its own to trigger the disease. Many believe that infectious agents are important environmental factors which help trigger T-cell activation. (P. Luppi and M. Trucco, Immunological Models of Type 1 Diabetes, 52 Horm. Res. 1 (1999)).

Systemic lupus erythematosus (SLE) is a non-organ specific auto-immune disease. The primary autoantigen responsible for the disease is not currently known. Although it was previously believed that DNA-AntiDNA complexes mediated the disease, it is now thought that nucleosomes and complement factor CLq play roles in the pathogenesis. (S. O. McLigeyo, Pathogenesis of Lupus Nephritis: a Review, 75 East Afr. Med. J, 628 (1998)).

Nephritis is a common complication of SLE. In this immune-mediated disease, nephritogenic autoantibodies which localize to the kidney are accompanied by activated macrophages and T cells as a result of enhanced, abnormal production of macrophage growth factors and cytokines. (M. H. Foster and V. R. Kelley, Lupus nephritis: Update on Pathogenesis and Disease Mechanisms, 19 Semin. Nephrol. 173 (1999)).

Rheumatoid arthritis is a chronic multisystem auto-immune inflammatory disease where an unknown autoantigen is presented to CD4+ T cells. The immune response primarily occurs in the synovial tissue and fluid of the joints. (Thomas R. MacDonald et al., Dendritic Cells and the Pathogenesis of Rheumatoid Arthritis, 66 J. Leukoc. Biol. 286 (1999)).

Although there are several treatments for the overt physiologically manifested symptoms of these disorders, an acute need exists for therapies which are directed toward altering the underlying mechanisms and biochemical pathways that cause these disorders. Moreover, techniques are needed to diagnose such disorders, as well as to identify specific mechanisms that are present in patients such that drug therapy, or surgical intervention, can be specifically selected in accord with the underlying pathologies of the disease.

SUMMARY OF THE INVENTION

A fundamental discovery underlying the present invention is the identification of specific biological pathways and biochemical mechanisms that underlie a number of auto-immune disorders. By detecting specific molecular markers, associated with such diseases, such as receptors and molecular signals, the present invention provides the ability to detect these pathways and mechanisms by measuring or detecting the markers individually, or by their byproducts or cellular modifications, and to understand the disease process that results from the underlying biological mechanism. Further-more, knowledge of the particular species and mechanisms as disclosed herein allows one of ordinary skill in the art to select or obtain compounds that interfere with the underlying mechanisms to be applied in a therapeutic or a clinical context.

One primary aspect of the present invention is to provide a method for alleviating antibody-mediated auto-immune diseases by administering to a mammal an effective amount of a compound that regulates the mechanism underlying the disease. In one embodiment, the therapeutic compound decreases the unique susceptibility of orbital fibroblasts to pro-inflammatory cytokines. In another embodiment, the therapeutic compound reduces the activity of T-lymphocytes that infiltrate orbital connective tissue and orbital resident fibroblasts. In specific embodiments, the therapeutic compound attenuates the signaling mechanisms of the FRAP/mTOR/$p70^{s6k}$ pathway. In another specific embodiment, the therapeutic compound down regulates activation of the PI3 kinase pathway. In a preferred embodiment, the compound is an allosteric modulator of a ligand that binds the IGF-1 receptor, and in the particular embodiments of RA or TAO, the compound blocks disease specific IgG from the IGF-1 receptor as a specific disease target. The compounds also include inhibitors of IL-16 and/or RANTES as defined by compounds that inhibit the expression, i.e. by inhibiting the production of message and/or protein to reduce IL-16 and RANTES activity. Some antibody-mediated inflammatory auto-immune disorders that can be treated by the invention are Thyroid-Associated Ophthalmology (TAO), vitiligo, leukemia, rheumatoid arthritis, lymphoma, lupus, pemphigus, adrenal failure, polyglandular failure, and Type I diabetes. A preferred embodiment of the invention is the treatment of Graves' disease (TAO) in human patients by administering an effective amount of an inhibitor of IL-16, such as PD098059, an hibitor of RANTES, such as SB203580, a combination thereof, or a compound that specifically attenuates the IGF-1 receptor, or a ligand thereof, preferably by blocking disease specific IgG. Rapamycin and PD098059 disrupt the signaling pathway that leads IL-16 expression or induction and therefore to lymphocyte infiltration and hyaluronic acid accumulation in orbital tissues, thereby alleviating the inflammation that causes protopsis in patients with TAO.

Other aspects of the present invention are diagnostic methods to determine whether a patient exhibits disease-specific antibody-activated fibroblasts and is thus a candidate for a specific treatment, including but not limited to the measuring serum levels of IL-16 and/or RANTES, measuring anti-IGF-1 antibodies, or detecting the activation of lymphocytes via IgG-mediated activation of T cells through the IGF-1 receptor. This diagnostic embodiment relies on the discovery that disease specific IgG from Graves' and RA patients activates lymphocytes directly and that the same activity for lymphocytes occurs in orbital and synovial fibroblasts as described below. Thus, the diagnostic utility of the invention is based in part on the ability to correlate disease-specific IgG with activated T cells and the identification of the IGF-1 receptor as the disease target. Based on this mechanism, disease specificity can be diagnosed by reacting IgG from a patient sample with any model that uses IGF-1 binding to detect downstream activation of lymphocytes or other components of the inflammatory auto-immune cascade.

One advantage of this diagnostic embodiment is an expansion of the cell type that may be used to measure the interaction of IgG in a patient sample with the IGF-1 receptor. Because the IGF-1 receptor is expressed on a broad number of cell types, a diagnostic can measure disease specific IgG in any cell type that detectably measures IGF-1 binding. Thus, IGF-1 receptor can be expressed in a non-human, model cell types by transfecting the cell with the gene for the IGF-1 receptor and a patient sample tested in such a model. As discussed herein, knowledge of the underlying mechanisms involved in the biochemical mechanisms of auto-immune disorders allows the ability to measure or diagnose these disorders at several points in the pathway underlying the disease. In the specific example of RA or TAO, enzyme-linked immunosorbent assay (ELISA) may be used to measure the levels of IL-16 and RANTES in biological samples induced by the binding of, for example, Graves' or RA IgG, and to compare the value to a control or normal value to determine the presence, absence, or severity of disease. The presence of specific markers or cell types, such as phenotype specific antibody-activated fibroblasts, may also be used as a factor in diagnosing an antibody-mediated inflammatory auto-immune disorder in the patient, in selecting a pharmaceutical surgical treatment for the disease, or predicting the severity and duration of the active phase of the disease.

BRIEF DESCRIPTION OF THE DRAWINGS

FIGS. 3A, 3B, and 3C show that the serum concentrations of IL-16 are elevated in patients with TAO (3A) and that IL-16 (3B) PGHS-2 protein (3C) can be detected in the orbital tissue of TAO patients.

FIG. 5 is an overview of one pathway implicated in antibody-mediated auto-immune disorders that may be alleviated or diagnosed according to the present invention.

FIG. 6A is unstimulate parental fibroblasts; FIG. 6B shows induced expression by INFα (100 u/ml in 46% of cells; and FIG. 6C shows extremely high levels of CD154 under basal culture conditions.

FIG. 9A is TAO tissue and shows strong CD40 expression while the control is (9B) negative.

FIG. 12A shows up-regulation of IL-16-dependent T-cell chemotaxis in TAO fibroblasts by Graves' IgG; FIG. 11B shows mimicking of Graves' IgG by IGF-1 in T-cell chemotaxis.

DETAILED DESCRIPTION OF THE INVENTION

Figure 1A:
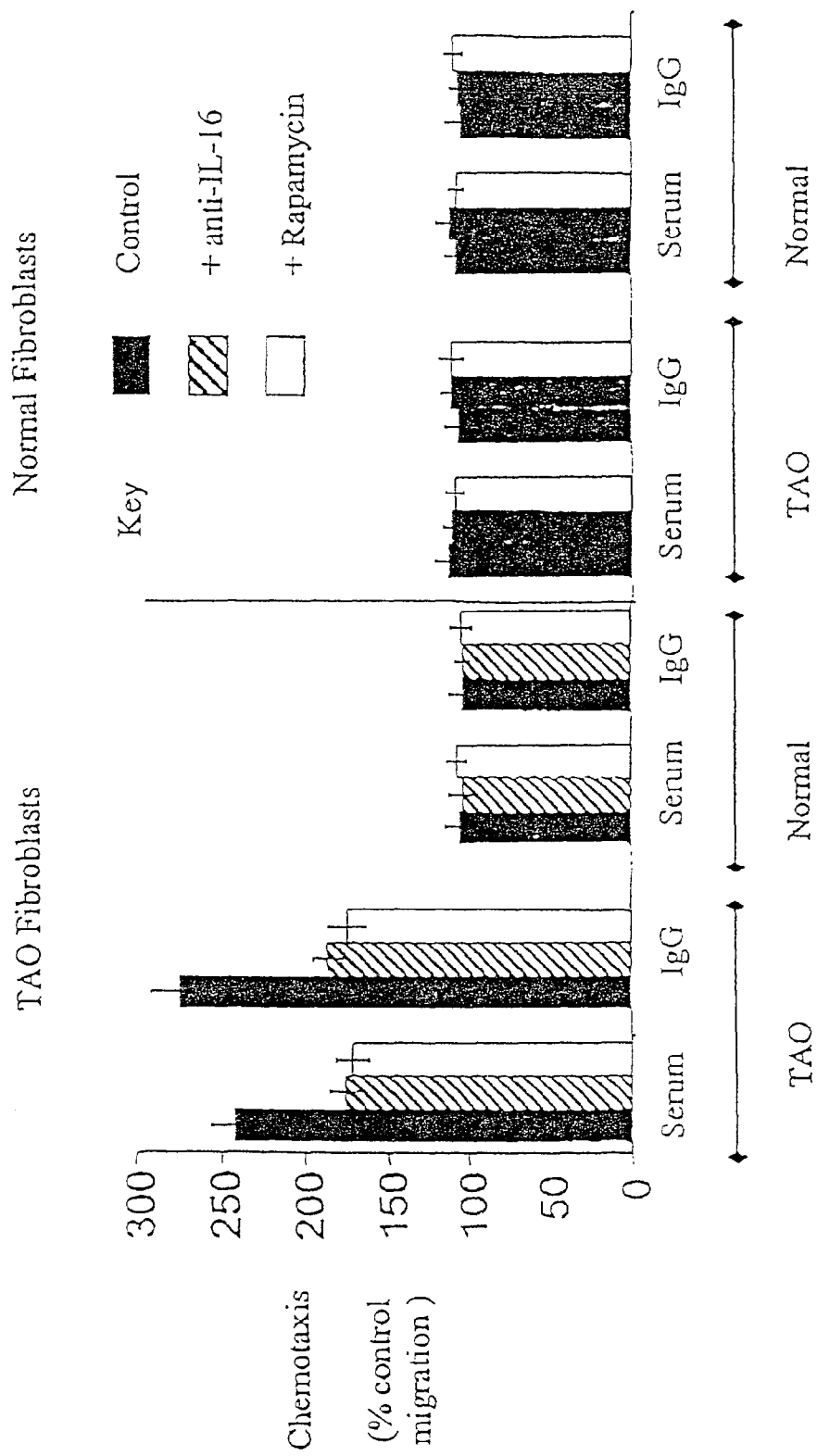
FIG. 1A shows that TAO fibroblasts exposed to either sera (1%) or to purified IgG (100 ng/ml) from donors with TAO exhibit a dramatic induction of IL-16 expression and release and that approximately 50% of the increase in chemoattractive activity is blocked by rapamycin.

As used herein, an "agonist" is a molecule that interacts with one or more receptors and is characterized by the specific ability to interact with the receptor and trigger the response pathway within a cell. As is demonstrated herein, an agonist increases or decreases a measurable parameter within a particular cell, such as the concentration of an expressed compound such as a chemokine, or modulates a specific function such as activation of a cell.

On the contrary, an "antagonist" refers to a molecule that interacts with a receptor, without stimulating the intercellular response pathway. Antagonists are generally identified by the ability to interact with the receptor and reduce the ability of the natural ligand to react with the receptor to stimulate the response pathway within the cell. For example, a compound that interferes with the binding of an IGF-1 ligand to the IGF-1 receptor is an IGF-1 antagonist and can be measured by determining the inhibition of cell functions that ordinarily accompany the binding of the IGF-1 receptor with its specific ligand.

An "allosteric modulator" of a ligand interacts with the receptor at a site other than which is recognized by the specific ligand and may act as either an agonist or an antagonist. Allosteric modulators are significant in the context of the present invention because such compounds may act as either an agonist or an antagonist for the specific interaction between the ligand and the receptor. For example, if an allosteric modulator acts as the antagonist, the compound reacts with the receptor to reduce the functional binding of the agonist. Thus, to the extent that the antibody-mediated inflammatory auto-immune diseases are controlled by the mechanisms described herein, the progress of the disease can be affected by providing an antagonist or an allosteric modulator of a specific receptor implicated in any of the pathways described herein.

As used herein "antibody-activated fibroblasts" are fibroblasts to which antibodies of the patient's immune system have bound, thereby up-regulating the synthesis and ultimate release of chemoattractant molecules, such as IL-16 and/or RANTES.

As used herein, "antibody-mediated inflammatory auto-immune disorder" means any disease in which antibody binding to the cells of a tissue of the patient is thought to lead to infiltration and proliferation of the inflammatory cells of the patient's immune system into those tissues. A non-exclusive list of such disorders includes Graves' disease and associated ophthalmopathy (TAO), Type I diabetes, Rheumatoid Arthritis, Lymphoma, Lupus (including SLE), Leukemia, Pemphigus, Vitiligo, Adrenal Failures, and Poly-glandular Failures.

As used herein a "biological sample" is a substance obtained from the patient's body. The particular "biological sample" selected will vary based on the disorder the patient is suspected of having and, accordingly, which biological sample is most likely to contain the analyte.

As used herein, the term "effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or their derivatives.

As used herein "elevated level" means the level of analyte which is greater by a statistically significant amount than the level of analyte present in a particular biological sample of a mammal that is not suffering from an antibody-mediated inflammatory auto-immune disorder. For Graves' disease, an elevated level of IL-16 is times the level of IL-16 in a mammal that is not suffering from Graves' disease. This differentiation enables the diagnostic elements of the present invention as disclosed herein.

As used herein, an "IL-16 inhibitor" is a compound that prevents the translation or transcription of the IL-16 gene, translation of IL-16 mRNA into protein, blocks the activation of pro-IL-16, or neutralizes the lymphocyte chemoattractive properties of IL-16 after it is released from the cell. Preferred translation inhibitors are rapamycin, PD98059, SB203580 (2'-Amino-3'-methoxyflavone; $C_{16}H_{13}NO_3$) Kültz, D., et al. 1998 J. Biol. Chem. 273, 13645, SB203580 Borsch-Haubold et al. J. Biol. Chem. 273, 28766 (1988) and wortmannin, which block the signaling pathways that culminate in the initiation of IL-16 translation. Caspase-3 cleaves bioactive IL-16 from the promolecule. Accordingly, caspase-3 inhibitors prevent the release of mature IL-16 and thereby inhibit IL-16 dependent lymphocytic chemotaxis. Anti-IL-16 antibodies bind bioactive IL-16 after its release from the cell, neutralizing the cell's IL-16-dependent lymphocyte chemoattractive ability.

As used herein a "patient" is a mammal suspected of having an antibody-mediated inflammatory auto-immune disorder. The patient is preferably human, but may also be another mammal.

As used herein, a "RANTES inhibitor" is a compound that prevents the translation or transcription of the RANTES gene, translation of a RANTES mRNA into protein, blocks the activation of RANTES, or neutralizes the lymphocyte chemoattractive properties of RANTES after it is released from the cell. The compound SB203580 is a preferred inhibitor of RANTES which blocks the signaling pathways leading to the initiation of RANTES expression. SB203580 is a selective and cell-permeable compound that acts by inhibiting the activation of P38 MAP kinase and phosphorylation of P38 MAP kinase substrates. SB203580 is reported to block the increase of MAP kinase activity produced by nerve growth factor. The compound inhibits cell growth and reverses the phenotype of ras-transformed BALB 3T3 mouse fibroblasts and rat kidney cells. Anti-RANTES antibodies bind bioactive RANTES after its release from the cell, neutralizing the cell's RANTES-dependent lymphocyte chemoattractive ability.

Cellular signal transduction is a fundamental biochemical mechanism whereby external stimuli regulate diverse cellular processes through signals that are conveyed to the cell and relayed to affect the internal biochemical mechanisms of the cell. To understand the disease process, the entire cascade of events must be determined whereby cells interact, signal one another, and ultimately manifest a disease. In many cases, the reaction whereby a ligand binds to a cell-surface receptor is the first step in a cascade of events or the initiation or regulation of a biological pathway that yields a cellular response. Each specific receptor recognizes one or a specific number of ligands, including polypeptides, nucleotide triphosphates, lipids, organic macromolecules, and derivatives and analogs of the foregoing. A compound or signal that modulates the activity of a receptor typically alters a cascade or biochemical pathway mediated by the receptor-ligand interaction as compared to a differential amount of the ligand-receptor interaction in comparison to a control. When such a cascade or a biochemical pathway is activated by an external stimulus such as a ligand-receptor binding event, the event may be detected or measured by a change in the concentration of another cell-related compound, or cell-based metabolic activity that reflects a change in the activity of the internal processes of the cell. By identifying the specific biochemical pathways that are activated in response to the receptor-ligand interaction, the receptor-ligand interaction can be measured, qualitatively or quantitatively, to analyze the function of the receptor or ligand.

In the context of the present invention, identification of the pathways involved in antibody-mediated inflammatory auto immune diseases provides the ability to diagnose the disease and intervene in the condition upon the identification of compounds that mediate any of the cascades or pathways that are identified pursuant to the present invention. As is revealed by the disclosure herein, the significant impediment to diagnose and treating such disorders is the absence of an understanding of these underlying biochemical reactions and their relationship to specific diseases. Once this understanding is obtained, the development of compounds to alter the biochemical reactions so identified is accomplished in many cases by traditional biochemical and chemical techniques.

The present invention is derived in part from the discovery of certain cellular mechanisms in auto-immune disorders and is derived from the discovery of the central role played by fibroblasts in the diverse physiological effects associated with auto-immune disorders, inflammation, and antibody-mediated auto immune disorders. Specifically, the role of orbital fibroblasts in initiating the inflammatory process through recruitment and activation of immune cells provides the insight through which other mechanisms can be identified. This specific insight into the role of fibroblasts is important because fibroblast cells are ubiquitous components of connective and other tissues, providing both structural needs for specific tissue types, but also providing a "gate keeper" function for tissue distress manifested by several diseases. Because of an extremely diverse repertoire of cytokine and chemokine production, fibroblasts recruit many types of cells, particularly those involved in an immune response, and condition the response of tissue to injury. Moreover, fibroblasts are known to produce important bioactive lipid mediators. Lipids are known structural components of cells, but have also been shown to play a fundamental role in intracellular signaling. Still further, the ability to differentiate orbital fibroblasts by specific phenotypes, provides additional information regarding the role of the fibroblast and the fibroblast-derived response to cytokine-mediated inflammatory conditions.

The various phenotypes exhibited by fibroblast cells may also determine the function of the cell in the pathogenesis of a disease, for example the role of the orbital fibroblast in the pathogenesis of TAO exhibited in many Graves' patients, or the role of the synovial fibroblast in RA, is derived in part from differential susceptibility to up-regulation of inflammatory cytokines. Thus, anatomic-site-specific activities of cytokines and fibroblasts explain the differentiation between orbital tissue, which may manifest Graves' disease, and most other anatomic areas of connective tissue, which do not manifest Graves' disease. The role of cytokines from immunocompetent cells in the pathogenesis of TAO is established by the presence in the TAO orbit of lymphocytes and other bone marrow-derived cells known to produce and release these molecules. In addition, the aberrant expression of class II MHC HLA-DR in affected tissue implies that interferon-γ is present at a high concentration. Based on this evidence, the orbital fibroblasts are shown to be particularly susceptible to the actions of both IL-1 and leukoregulin. Therefore, in the specific example of TAO, the foregoing mechanisms underlie the disease resulting from alterations in orbital fibroblasts, acting as sentinel cells for the several mechanisms described herein, and as the target for the IgG-based immunologic reaction in TAO.

Fibroblasts also exhibit an important activational pathway. CD40 is a member of the TNF-α receptor family and its cDNA shares sequence identity with the low affinity nerve growth factor receptor, TNFα receptors 1 and 2 Fas/Apo1, which can trigger apoptosis in lymphocytes. The structural attributes common to all these receptors include 3-4 cysteine-rich tandem repeats of approximately 40 amino acids each in the extracellular, ligand binding portion of these proteins. CD40 appears to function like a traditional cytokine receptor and is expressed on cells of the B lineage. Specifically, CD40 is expressed by B cell precursors in the adult bone marrow, in fetal liver and marrow, in epithelial cells, and in and in essentially all mature, normal and malignant B cells. With respect to auto-immune disorders, antigen-presenting cells capable of activating T lymphocytes, such as dendritic cells and monocytes/macrophages, can also display CD40. Human orbital fibroblasts express CD40 and are an important signaling pathway relevant to the pathogenesis of TAO. In fact, fibroblasts from most connective tissue depots do not express CD40, however, CD40 is expressed at high levels on orbital fibroblasts, especially following treatment with interferon γ. When CD40 is ligated with recombinant CD 154, an unidentified set of molecular events leads to the activation of several important down-stream genes. Both Thy-1$^+$ and Thy-1$^-$ fibroblasts exhibit bimodal CD40 expression when treated with interferon γ.

CD154, also known as CD40 ligand, is a member of the TNF-α superfamily, initially found expressed on T lymphocytes but also detected on mast cells and platelets. Although CD154 expression is thought to be restricted to immunocompetent cells and to represent a critical element displayed by T cells that orchestrates B cell maturation and survival, TAO orbital fibroblasts, besides displaying CD40, express very high levels of CD154 under basal culture conditions, implying orbital fibroblast autoactivation, and in the context of TAO, a direct impact on B cell activation and survival. These data reveal a role for activated T lymphocytes infiltration of orbital connective tissue and resident fibroblasts and the activation of these fibroblasts through CD40 yields remodeling of tissue and inflammation that occurs in TAO. Because fibroblasts from most tissues of the body fail to express CD40 or respond to CD154, this CD40/CD154 reaction selectively targets specific fibroblast populations, such as those in the orbit.

IL-16, in concert with RANTES, a c-c chemokine, are the principal lymphocyte chemoattractants expressed and released by cytokine-activated human fibroblasts (Sciaky, D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164 (7):3806-14, 2000), including orbital fibroblasts in TAO and synovial fibroblasts in RA. Moreover, IL-16 and RANTES synthesis in RA synovial and TAO orbital fibroblasts, but not in fibroblasts from orbits, dermal, or other anatomic sites of subjects without disease, are an important target for TSI-dependent up-regulation, and thus may represent the critical pathway through which disease is initiated. An important step in the discovery of the present invention was the elucidation of the critical mechanisms through which IL-16 and RANTES expression in fibroblasts is induced through disease specific binding of IgG to the IGF-1 receptor because this mechanism provides the disease specific target to which therapeutic modalities may be applied and represent a key target for diagnosis of the underlying disease.

The regulation of protein translation involves a cascade of kinases that is inhibited by the immunosuppressive drug, rapamycin. It has been demonstrated recently that the translation of many, although not all mRNAs, is regulated by a pathway that culminates in a complex of three protein components that are termed, in aggregate, eukaryotic translation initiation factor-4E (eIF-4E). This complex interacts with the m7 cap of target mRNAs and recruits the 40S ribosomal subunit. The activity of eIF-4E is governed, in part, by a family of inhibitory polypeptides termed 4E-BPs. These 4E-BPs, when under-phosphorylated, bind and inhibit the activities of eIF-4E. But when they become phosphorylated at crucial amino acids their binding to eIF-4E is attenuated. Immediately up-stream from the 4E-BPs and proximately responsible for their phosphorylation is the FRAP/mTOR kinase. It is of significant importance to this proposal that the upstream pathway leading to 4E-BP phosphorylations is sensitive to the immunosuppressive drug, rapamycin. eIF-4E activity can also be regulated through gene transcription and by varying the relative levels of phosphorylation of eIF-4E itself. Cytokines and growth factors eliciting eIF-4E phosphorylations act, at least in part, through protein kinase C and MAP kinase that are insensitive to rapamycin. Another component of mRNA translational regulation which is sensitive to rapamycin and which targets a subset of mRNAs for translation, through an as yet undefined mechanism, is termed $p70^{s6k}$. Currently, nothing is known about any of these pathways that regulate mRNA translation in orbital fibroblasts. However, applicants have found that the rapamycin-sensitive pathway(s) are of critical importance to the activation of IL-16 mediated lymphocyte signaling by TSI in these fibroblasts.

TAO is also characterized by a disordered accumulation of hyaluronan in inflammation in orbital soft tissues. Applicants have shown that fibroblasts derived from orbital endomysial and adipose/connective tissue are identical but differ dramatically from those emanating from outside the orbit (skin, subcutaneous, omental, breast and skeletal muscle). Orbital fibroblasts express a characteristic pattern of gangliosides and surface receptors. As is described in more detail herein, orbital fibroblasts are heterogeneous with regard to the surface display of Thy-1 and can be segregated into discrete populations on that basis. They have been characterized by us as expressing collagens I and III, fibronectin and vimentin but not markers of endothelial, epithelial or smooth muscle cells. Orbital fibroblasts engender many of the identifying features associated with fibroblasts and applicants have demonstrated an ultrastructure identical to that of non-orbital fibroblasts (Henrikson, R. C. and Smith, T. J.: Ultrastructure of cultured human orbital fibroblasts. *Cell Tis. Res.* 278:629-6331, 1994).

Applicants have also recently made a number of directly relevant observations of the disordered accumulation of hyaluronan in TAO. Orbital fibroblasts synthesize less hyaluronan constitutively than do dermal fibroblasts (Smith, T. J., Bahn, R. S. and Gorman, C. A.: Hormonal regulation of hyaluronate synthesis in cultured human fibroblasts: evidence for differences between retroocular and dermal fibroblasts. *J. Clin. Endocrinol. Metab.* 69:1019-1023, 1989). However, interferon-γ can modestly upregulate hyaluronan synthesis in orbital but not dermal fibroblasts (Smith, T. J., Bahn, R. S., Gorman, C. A. and Cheavens, M.: Stimulation of glycosaminoglycan accumulation by interferon gamma in cultured human retroocular fibroblasts. *J. Clin. Endocrinol. Metab.* 72:1169-1171, 1991). Upon investigation, applicants found that leukoregulin, a T cell-derived cytokine, and IL-1β were found to dramatically up-regulate glycosaminoglycan synthesis in orbital fibroblasts (up to 15-fold above baseline). The macromolecular material was sensitive to *Streptomyces* hyaluronidase digestion, defining it as hyaluronan (Smith, T. J., Wang, H.-S. and Evans, C. H.: Leukoregulin is a potent inducer of hyaluronan synthesis in cultured orbital fibroblasts. *Am. J. Physiol.* 268:C382-C388, 1995, appended). The increase was substantially greater in magnitude than that observed in dermal fibroblast strains from the same donors (3-fold) and on the basis of pulse-chase studies could be attributed to changes in net synthesis. Thus, applicants have demonstrated an anatomic-site-preferential induction of hyaluronan synthesis in orbital fibroblasts.

Applicants have used cloned UDP-glucose dehydrogenase cDNAs to examine the expression and inducibility of this enzyme in orbital fibroblasts (Spicer, A. P., Kaback, L. A., Smith, T. J. and Seldin, M. F.: Molecular cloning, and characterization of the human and mouse UDP-glucose dehydrogenase genes. *J. Biol. Chem;* 273:25117-25124, 1998, appended). Inducible mRNA expression in TAO orbital fibroblasts with IL-1β and leukoregulin is unexpected because it had been assumed that this enzymatic step was not regulated. Mechanistic insight into the normal and pathological regulation of the hyaluronan synthetic pathway suggests multiple enzymes in the hyaluronan synthetic cascade in the orbit can be regulated in orbital fibroblasts by extracellular cytokine messengers which are produced by infiltrating T-lymphocytes.

The pathogenesis of both RA and TAO, where T lymphocyte infiltration is a hallmark, involve the mechanisms of connective tissue lymphocyte signaling. Referring to FIG. 1, IL-16, a CD4-specific ligand already associated with inflammation and autoimmunity, is a key participant in the disease process. All human fibroblasts thus far examined express high levels of IL-16 mRNA under basal culture conditions but no detectable IL-16 pro-molecule or mature protein is synthesized until the cells are activated with a pro-inflammatory cytokine such as IL-1β, leukoregulin and CD154. This pattern of IL-16 expression differs in various cell types, including CD8+ lymphocytes, mast cells, and bronchial epithelium. The amount of IL-16 synthesized by fibroblasts is several-fold greater, on a per cell basis than that in these other cell types and it appears to be an important lymphocyte chemoattractant, in concert with RANTES, produced by fibroblasts.

IL-1 activates the translation of the pre-formed IL-16 mRNA but steady-state levels of the transcript remain constant. IL-1β also activates caspase-3 in fibroblasts and inhibiting this enzyme precludes the cleavage of mature IL-16 protein from the pro-molecule or its release from the cell.

All human fibroblasts thus far examined, including many from anatomic regions not affected in Graves' disease, express the TSH-R and have begun to explore the functional consequences of this receptor expression on orbital fibroblasts (Bell, A., Grunder, L., Gagnon, A., Parikh, S. J., Smith, T. J. and Sorisky, A.: Expression of functional TSH receptor protein in human abdominal preadipocytes and orbital fibroblasts in primary culture. *Am. J. Physiol.* ((279: C335-340, 2000)). As discussed in Example 4, TAO fibroblasts exposed to either sera (1%) or to purified IgG (100 ng/ml) from donors with TAO exhibit a dramatic induction of IL-16 expression and release (See FIGS. 3A-3C). Notably, fibroblasts from donors without known thyroid disease fail to exhibit this IL-16 response. Approximately 50-70% of the T lymphocyte chemoattractive activity released from IL-1 R-treated fibroblasts can be neutralized with an IL-16 blocking antibody. As demonstrated in Example 1, the remaining activity is susceptible to anti-RANTES antibodies, and, when neutralizing antibodies to both IL-16 and RANTES are added, virtually no chemoattractant activity remains.

As is further demonstrated in FIG. 1, approximately 50% of the increase in chemoattractive activity is blocked by rapamycin (20 nM), a specific inhibitor of the FRAP/mTOR pathway. When anti-IL-16 antibodies were added to rapamycin-treated fibroblast cultures, no further decrease in chemoattraction occurred, suggesting that rapamycin is blocking the IL-16-dependent lymphocyte migration activity. Levels of IL-16, assessed by ELISA, increase from being undetectable (in controls and TSI treated normal orbital cultures) to 538±51 pg/ml in the TSI-treated TAO cultures. This increase was blocked completely with rapamycin (20 nM).

Figure 2A:
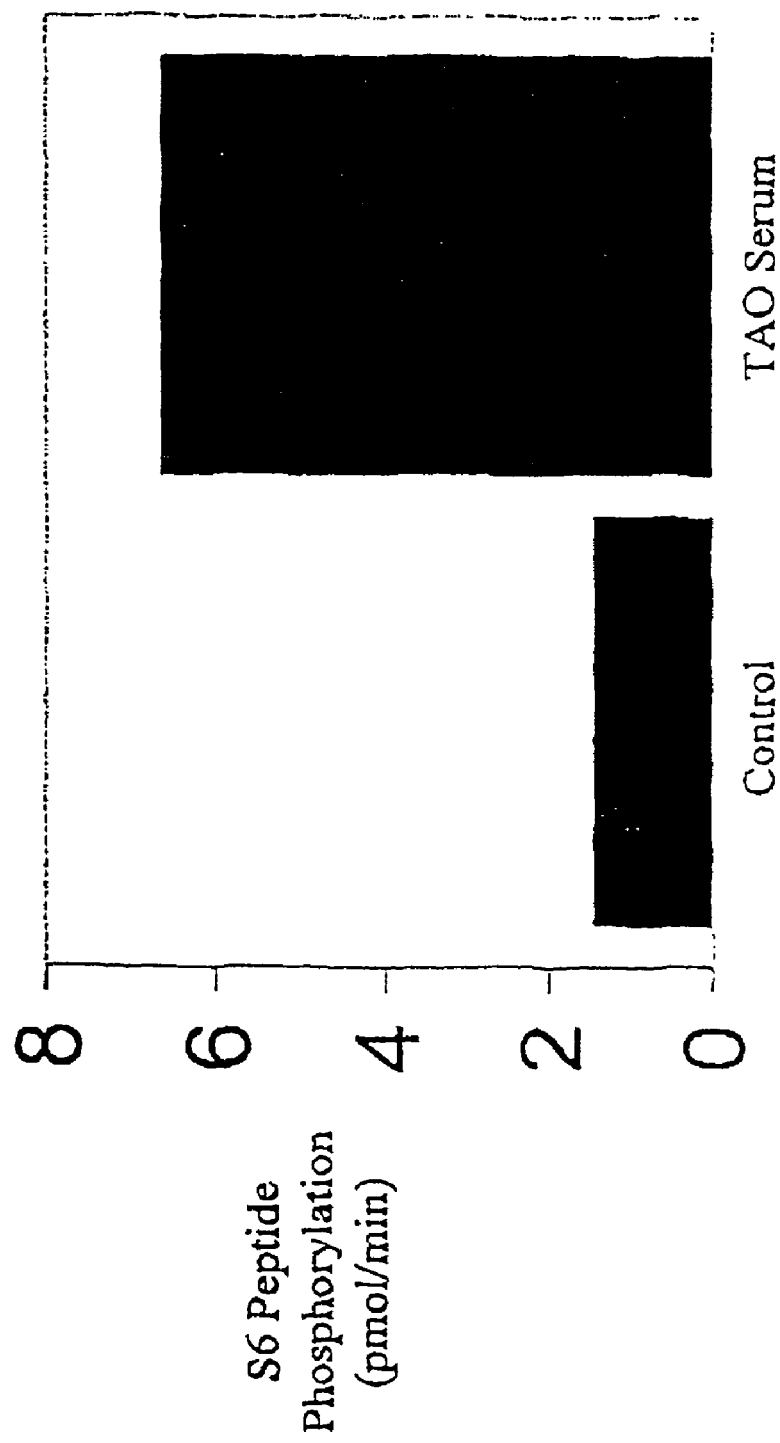
FIGS. 2A and 2B show activation of $p70^{s6K}$ by TSI 92A) and a schematic pathway of phosphorylation inhibition in a pathway that regulates, in part, translation of mRNA to protein.
Figure 2B:
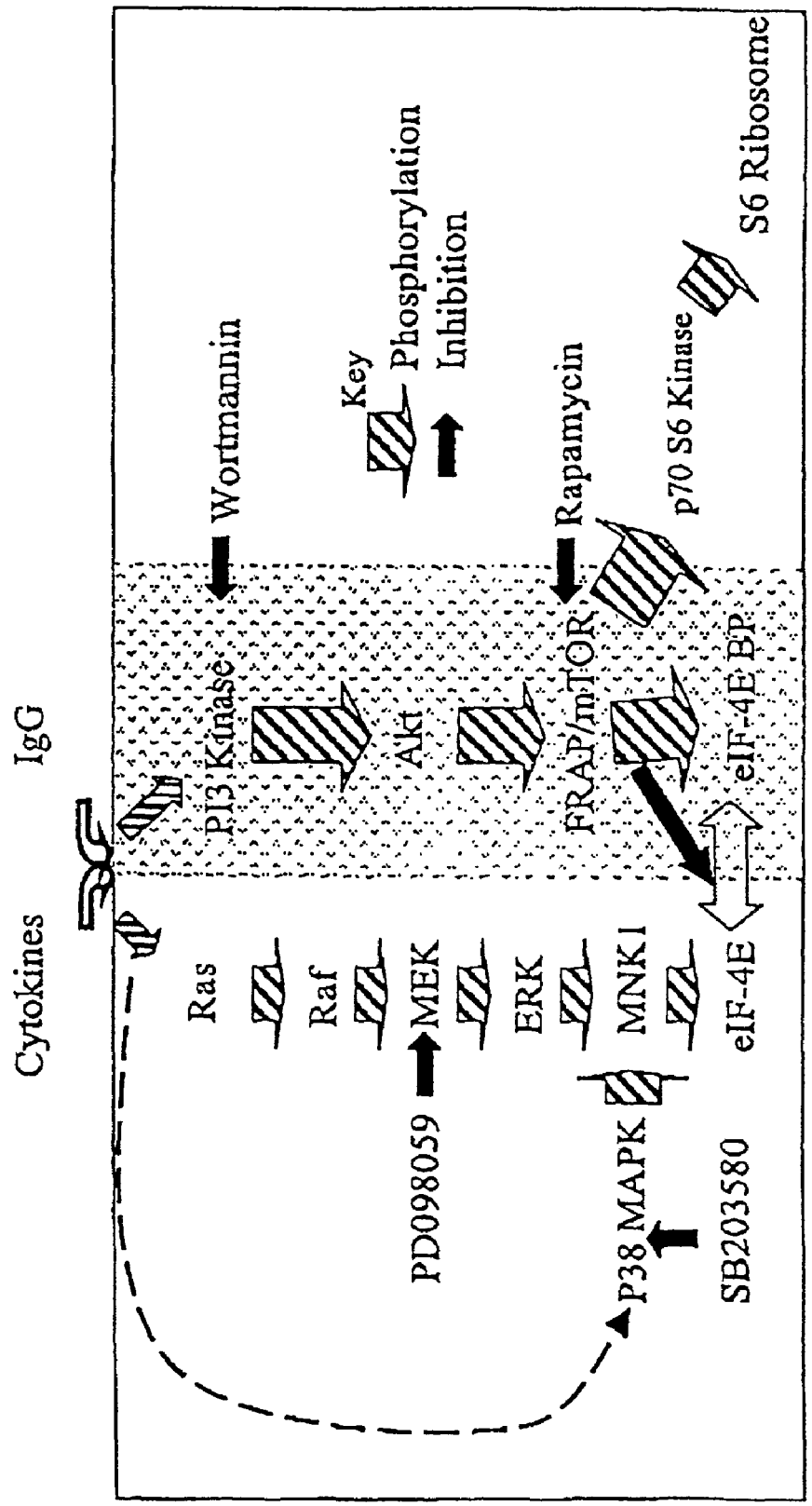

As the data in FIG. 2A indicate, TSI activates $p70^{s6k}$. Levels of S6 peptide phosphorylation are consistently increased by at least 6-fold above controls after 1-3 hours of treatment. In contrast, IgG from individuals without Graves' disease fails to elicit either the IL-16 response or an activation of $p70^{s6k}$. Moreover, recombinant TSH does not activate the $p70^{s6k}$ pathway or induce IL-16 production. The effect of TSI on IL-16 synthesis is time-dependent and has been observed with sera and purified IgG from 6 different patients with severe TAO and has been replicated using three different TAO fibroblast strains. IL-16 synthesis-activating properties can be removed from TAO sera with protein A and can be eluted from protein A beads, suggesting that IgG is conveying both activities and that this mechanism induces lymphocyte activation and migration.

Pursuant to this invention, IL-16 and RANTES are demonstrated to be relevant to the pathogenesis of TAO. Measurement of IL-16 in the sera of 7 individuals with severe, active TAO shows that the levels of this chemoattractant are consistently elevated compared to control sera from individuals without known thyroid disease (1102±356 pg1ml in TAO vs. 97±18 in controls; 11-fold elevation) (see FIG. 3A). Moreover, thin-sections of TAO orbital connective tissue exhibits specific immunostaining with an IL-16-specific polyclonal antibody (See FIG. 3B). Thus, IL-16 levels in orbital tissue and serum are increased considerably in TAO.

Based on the current results, Graves' disease-specific IgG, invariably found in individuals with TAO, interacts with orbital fibroblasts to induce IL-16 protein expression. This results in lymphocyte trafficking to the orbit. This invention yields a molecular rationale for why lymphocytes infiltrate the orbit in TAO—an important step in stimulating the cytokine-induced hyaluronic acid synthesis pathway.

Figure 4:
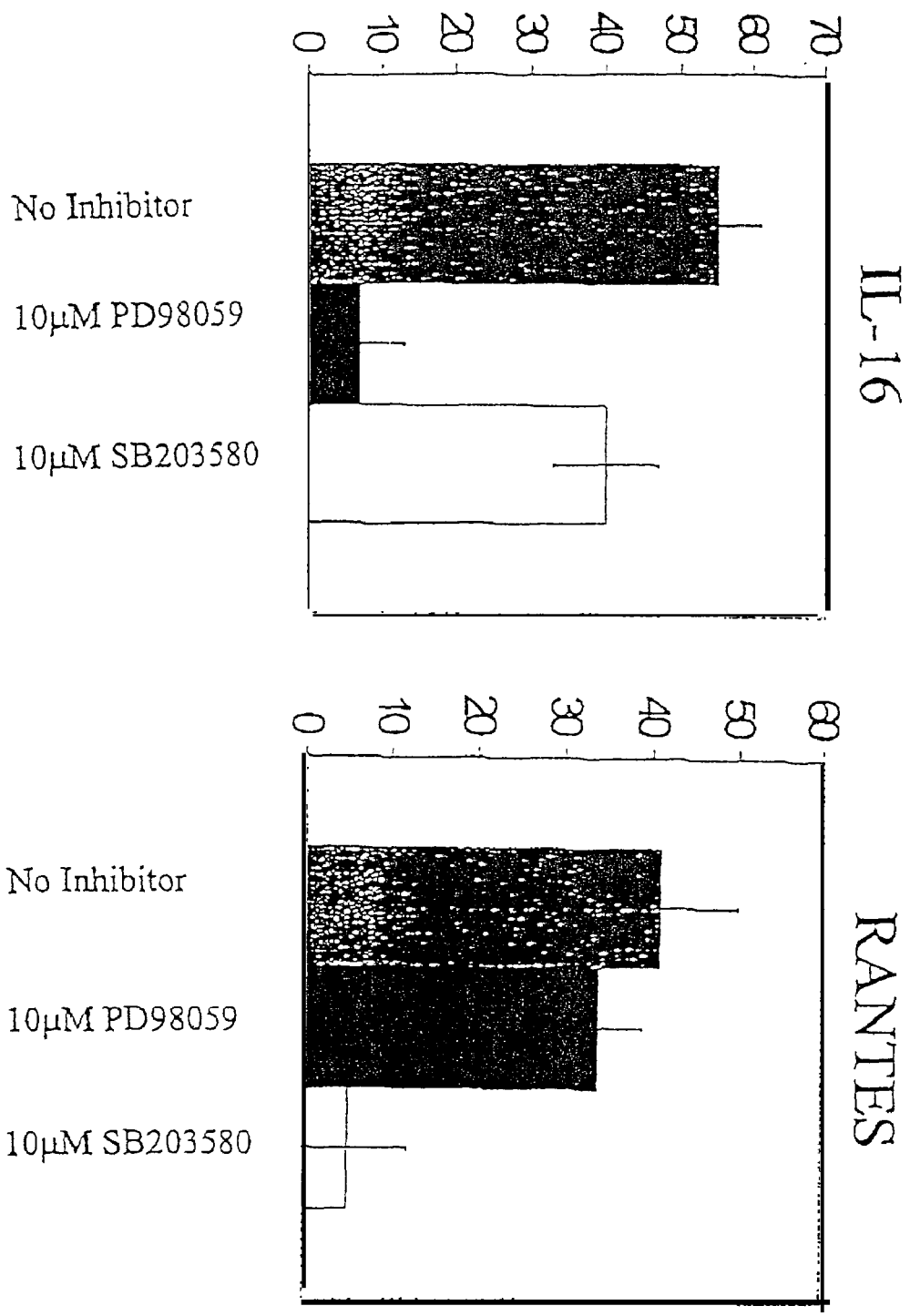
FIG. 4 shows the inhibition of expression of SB203580 and PD098059 on IL-16 and RANTES.

Referring to FIG. 5, these findings on the role of IL-16 and RANTES in the fibroblast/lymphocyte inflammation cascade provide options for therapies for TAO, RA and other antibody-mediated inflammatory auto-immune disorders. The method of the therapeutic aspect of the invention involves inhibiting the activity of the two chemoattractant molecules that are substantial contributors to the inflammation cascade, IL-16 and RANTES. IL-16 inhibitors include, but are not limited to, rapamycin, wortmannin, caspase-3 inhibitor, and anti-IL-16 antibody. RANTES inhibitors include, but are not limited to, SB203580, and anti-RANTES antibody. Referring to FIG. 4, the data demonstrate the action of SB203580 and PD098059 on IL-16 and RANTES. These compounds either block translation of the chemoattractant molecules, prevent release of chemoattractant molecules from the cell after they are translated, or neutralize the chemoattractant molecules' ability to cause lymphocytic chemotaxis after they are released.

Rapamycin, wortmannin and PD098059 are inhibitors which block the signaling pathway that culminates in the initiation of IL-16 translation. Recent studies indicate that rapamycin and wortmannin accomplish this by inhibiting the phosphorylation of a key protein in a pathway that regulates, among other things, the translation of mRNA to protein. In their unphosphorylated form, these 4E-BPs bind and inhibit translation initiation factor-4E, which is responsible for recruitment of the 40S ribosomal subunit. Rapamycin also acts on $p70^{s6k}$, another component of mRNA translational regulation, which targets a subset of mRNA for translation through an as yet undefined mechanism.

Caspase-3 inhibitor prevents the cleavage of bioactive IL-16 from its promolecule, thereby blocking release from the cell. The protein sequence of the caspase-3 inhibitor is (Ac-Asp-Glu-Val-Asp-aldehyde)[3], as described in Sciaky, D. et al., *J. Immunol.* 164(7):3806-14, 2000.

Anti-IL-16 and anti-RANTES antibodies neutralize the chemoattractant characteristics of IL-16 and RANTES, respectively, after they are released from the cell. In a preferred embodiment of the invention in which the antibodies are administered to a human, humanized anti-IL-16 and humanized anti-RANTES are prepared in a manner similar to the method described in U.S. Pat. No. 6,054,297. Also, any compound acting as an antagonist of the IGF-1 receptor to block disease specific IgG is a preferred embodiment for a therapeutic compound.

Any suitable dosage of the compounds may be given in the method of the invention. Dosage levels and requirements are well recognized by those of ordinary skill in the art. As one of ordinary skill in the art will appreciate, lower or higher doses may be required depending on particular factors. For instance, specific dosage and treatment regimens will depend on facts such as the mammal's general health profile, the type of antibody-mediated auto-immune disorder being treated, the severity and course of the patient's disorder, and the judgment of the treating physician.

Dosage forms of the compounds of this invention include pharmaceutically acceptable carriers known to those of ordinary skill in the art. Pharmaceutically acceptable components are those that are suitable for use with mammals without undue adverse side effects (such as toxicity, irritation, and allergic response) commensurate with a reasonable benefit/risk ratio. The carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules and bulk powders. Tablets may contain suitable binders, lubricants, diluents, disintegrating agents, coloring agents, flavoring agents, flow-inducing agents and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners and melting agents. Parenteral and intravenous forms may also include isotonic salts and other materials to make them compatible with the type of injection or delivery system chosen.

The method of administration can be any suitable method which effectively alleviates the particular antibody-mediated inflammatory auto immune disorder being treated. Possible ways in which the treatment may be administered are orally, rectally, parenterally, enterically, subcutaneously, transdermally, peritoneally, or intravenously.

In addition to its therapeutic aspects, the present invention also relates to a diagnostic method for detecting the presence of antibody-activated fibroblasts in the patient. Applicants believe that several auto immune diseases or disorders are associated with antibody-activated fibroblasts. Applicants have shown that increased activation of fibroblasts by autoantibodies can be monitored by determining the levels of IL-16 and/or RANTES production in a patient. Altered levels of these chemoattractants can be detected in various biological samples in mammals, preferably humans. Levels of IL-16 and/or RANTES may be monitored in a patient, using standard techniques, as an indication of the deleterious aspects of the disease condition. Biological samples, including but not limited to serum, vitreous humor, aqueous humor, synovial fluid, and tissue, will be drawn from the patient using standard techniques. Particularly preferred are serum samples. The measurement of the IL-16 and RANTES levels may be monitored using any method possible to detect the levels of these proteins in biological samples. A preferred method of analysis is by ELISA as described in Sciaky, D. et al., *J. Immunol.* 164(7):3806-14, 2000. An ELISA specific for IL-16 can be used to assess the levels released by fibroblasts as described previously in Lim, K. G. et al., *J. Immunol.* 156(7): 2566-70, 1996. An ELISA specific for RANTES can be used according to the manufacturer's specification (BioSource Intl., Camarillo, Calif.).

The following examples merely illustrate the invention, and should not be construed as limiting the invention to any particular embodiment.

EXAMPLE 1

Production of IL-16 and RANTES by Orbital Fibroblasts Upon Stimulation by TSI and Resultant Chemoattractant Activity Orbital tissue in TAO becomes inflamed and infiltrated with lymphocytes and mast cells. Although the reason why immunologically competent cells are trafficked to the orbit is uncertain, applicants have presented preliminary evidence that the production of the CD4-specific chemoattractant, IL-16, is dramatically induced by TSI in TAO but not in normal orbital fibroblasts, (see FIG. 1). This experiment demonstrates that the expression of chemoattractants in the TAO orbit is the basis for T lymphocyte recruitment, and that the 50% of chemoattractive activity not accounted for by IL-16 is RANTES. This experiment demonstrates the role of IL-16 and RANTES in the lymphocyte migration activity emanating from fibroblasts by neutralization of these proteins with specific antibodies.

The general migration assay is described in detail in Sciaky, D., et al., "Cultured human fibroblasts express constitutive IL-16 mRNA: Cytokine induction of active IL-16 protein synthesis through a caspase-3-dependent mechanism," *J. Immunol.* 164(7):3806-14 (2000), hereby incorporated fully by reference. Briefly, fibroblasts from TAO and normal orbital tissue were seeded in 24-well arrays and grown to confluence. Monolayers were shifted containing 1% FBS to which nothing, purified normal or TAO IgG was added for various time intervals. Medium was collected and stored until use at $-80°$ C. Chemotaxis was examined using Boyden chambers to which NWNA-T lymphocytes were added as the cellular targets. 50 µl cell suspension ($10^7$ cells/ml) were placed in the upper compartments of 48-well micro-chemotaxis chambers separated from 32 µl of serum samples by 8 µm micropore nitrocellulose filters (Neuroprobe). These were incubated at $37°$ C. in 5% $CO_2$ environment for 3 hr. Filters were fixed, stained with hematoxylin, dehydrated, mounted on glass slides and viewed by light microscopy. Lymphocyte migration was quantified by counting the total number of cells migrating beyond a fixed depth. This depth was set to routinely identify a baseline migration under control conditions of 10-15 cells per high power field. Five such fields were counted in duplicate for each sample and the means±SD were calculated and expressed as percentage values of baseline cell migration in control buffer alone (100%). For each set of experimental conditions, at least three separate determinations were performed. Differences between experimental groups were analyzed by the Student t test using absolute values obtained for lymphocyte migration and statistical difference was accepted at the 95% level of confidence.

To assess specificity for IL-16, experiments were conducted by incubating samples of culture media for 15 min with neutralizing concentrations of anti-IL-16 MAB (clone 14. 1, 10 µg/ml), which blocks the chemotactic activity of 50 ng/ml of rIL-16. Anti-RANTES MAB (5 µg/ml) having an $ND_{50}$ of 200 ng/ml rRANTES was used to neutralize RANTES as described in Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806-14, 2000).

The levels of IL-16 and RANTES were then assessed with specific ELISAs. The ELISA assay for IL-16 is performed essentially as discussed in Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806-14, 2000). An ELISA (BioSource) for RANTES was performed according to the manufacturer's instructions. In an analysis of over a dozen strains, TAO specific IgG elicit substantial induction of IL-16 and RANTES and in no case were normal fibroblasts so affected.

Whether TSIs up-regulate IL-16 at a pre-translational level was assessed by performing northern blot analysis using a probe generated from a full-length cDNA as described in the Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806-14, 2000). A similar northern blot analysis was performed using a full length cDNA probe for RANTES.

As demonstrated by the data, IL-16 and RANTES are the dominant components of T lymphocyte chemoattraction generated by TSI-activated TAO fibroblasts.

EXAMPLE 2

Demonstration of Identity between TSI and the IgG TAO Serum Factor which Activates TAO Ocular Fibroblasts As described above, applicants have found that a component of TAO serum, binding to protein A, activates the synthesis and release of mature IL-16 and other chemoattractive activity from TAO orbital fibroblasts. This activity is manifested only in TAO but not normal orbital fibroblasts. This experiment demonstrates that the fibroblast-activating IgG belongs to the same subclass as classic TSI, which is an IgG1, and presents other evidence in support of the proposition that the component of TAO serum which activates TAO fibroblasts is, in fact, TSI.

mine whether cAMP generation and thyroid hormone synthesis (classical TSI activities) are up-regulated.

The data demonstrate that the active serum component is an IgG, as verified in 5 additional sera samples from patients with TAO. As can be seen from the control sera from normal control donors without known thyroid disease, the immunoglobulin constituent of the TAO serum responsible for fibroblast activation is specific to Graves' disease.

EXAMPLE 3

Graves' Disease Specific-IgG Induction of IL-16 Expression and Release Involves a Rapamycin-Sensitive Pathway As noted above, Graves' disease specific-IgG induces IL-16 and RANTES expression in fibroblasts by binding an epitope of the IGF-1 receptor on the cell surface. This reaction initiates protein synthesis through the activation of one or more signaling pathways. The FRAP/mTOR pathway and the activation of $p70^{s6k}$, a serine/threonine kinase, play central roles in mediating the effects provoked by factors acting at the cell surface. A prominent characteristic of this pathway is its susceptibility to inhibition by the macrolide, rapamycin. This compound, at a concentration of 20 nM, can block ca 50% of the chemoattractive activity elicited by Graves'-IgG, coinciding with an attenuation of IL-16-dependent T cell migration (See Table I).

TABLE I

Effects of rapamycin and dexamethasone on IL-16 and RANTES synthesis and T lymphocyte migration activity provoked by IgG in fibroblasts from patients with GD.

|  | Lymphocyte migration (% control)[A] | +anti-IL-16 | +anti-RANTES | +Both antibodies | IL-16 (pg/ml)[B] | RANTES (pg/ml)[C] |
|---|---|---|---|---|---|---|
| Experiment 1 |  |  |  |  |  |  |
| GD-IgG | 274 ± 16 | 186 ± 9 | 217 ± 9 | 162 ± 8 | 538 ± 51 | 462 ± 68 |
| GD-IgG + rapamycin | 190 ± 10 | 184 ± 12 | 157 ± 9 | 155 ± 11 | ND | 449 ± 73 |
| Experiment 2 |  |  |  |  |  |  |
| GD-IgG | 195 ± 11 | 135 ± 9 | 159 ± 7 |  | 47 ± 7 | 26 ± 8 |
| GD-IgG + dexamethasone | 121 ± 8 | 117 ± 9 | 118 ± 8 |  | ND | ND |

Confluent monolayers of fibroblasts were treated with nothing, GD-IgG (100 ng/ml) without or with rapamycin (20 nM) or dexamethasone (10 nM) for 24 hr.
The conditioned medium was then subjected to the T cell migration assay, as described in Methods without or with anti-IL-16 (10 μg/ml) and/or anti RANTES (5 μg/ml) neutralizing antibodies.
Another aliquot of medium was subjected to the cytokine-specific ELISAs described. Data are expressed as the mean ± SD of 3 independent determinations.
[A]Migration is expressed as a percent of control, the activity levels of which were found in untreated fibroblast cultures. Migration of greater than 135% was significant at 5% confidence limit.
[B]Limits of detection 20 pg/ml.
[C]Limits of detection 15 pg/ml.

First, sera was incubated with beads containing anti-heavy chain-specific antibodies, which verified that the immunoglobulin is IgG and not IgM. The adsorbed IgG was eluted either with high salt concentrations or low pH. Aliquots of the material were then passed over a series of IgG isotype-specific columns commercially available from Pharmingen, R & D and Sigma. The purity of the materials adsorbed to these affinity matrices was verified by subjecting them to isotype-specific ELISAs (Sigma).

Figure 1B:
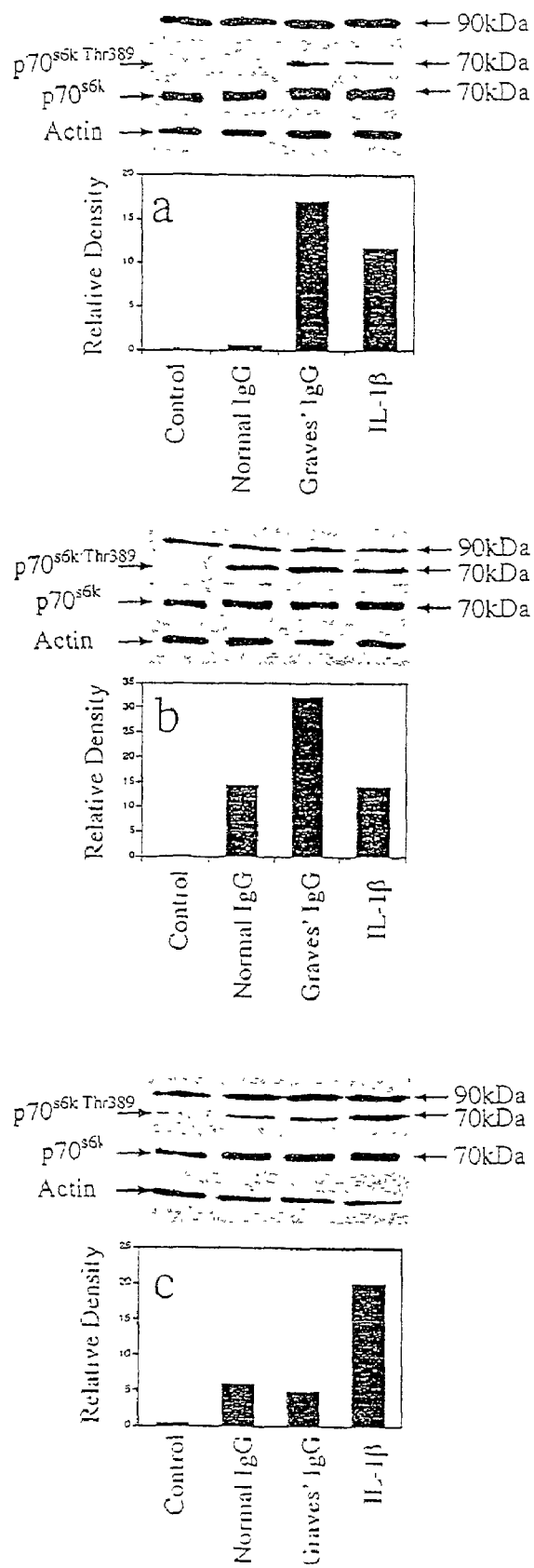
FIG. 1B shows that GD-IgG rapidly activates $p70^{s6k}$ Thr389 phosphorylation is GD fibroblasts. Confluent monolayers of orbital fibroblasts from two patients with GD (A and B) or a single donor with normal orbital tissue (C) were incubated with nothing (control), normal IgG (100 ng/ml), GD-IgG (100 ng/ml) or IL-1β (10 ng/ml for 15 minutes, cells were rinsed and harvested in lysis buffer. Equivalent amounts of protein were subjected to western blot analysis with pan anti-$p70^{s6k}$, phospho-specific anti-$p70^{s6k}$ Thr389, or anti-actin antibodies. Signals were generated with the ECL method. Column heights represent $p70^{s6k}$ Thr389 signal densities corrected for their respective actin levels.

At each step of the purification process, an aliquot was assayed for IL-16-inducing activity in TAO fibroblasts to verify the presence of activity. The aliquot was also assayed for activity in the primary thyrocyte culture system described in Gianoukakis, A. G., et al., "Prostaglandin endoperoxide H synthase expression in cultured thyroid epithelial cells: Potential contributions to glandular inflammation" to deter- The induction of IL-16 protein by Graves' IgG is blocked by rapamycin whereas that of RANTES is not. Referring to FIG. 1B, to determine whether Graves' IgG increased levels of activated $p70^{s6k}$, Graves'-IgG (100 ng/ml) is determined by western blot immunoblot analysis with a primary antibody specific for $p70^{s6k}$ phosphorylated at $Thr^{389}$. IgG from control subjects (100 ng/ml) also increased phosphorylated $p70^{s6k}$, but the levels are considerably lower. Moreover, normal fibroblasts challenged with either Graves' IgG or control IgG failed to exhibit substantial $p70^{s6k}$ activation. These findings suggest that $p70^{s6k}$ activation by IgG may alone be insufficient to up-regulate IL-16 expression. Given the ability of rapamycin to block, the activation of $p70^{s6k}$ appears essential for the induction by Graves' IgG of IL-16 fibroblasts.

Glucocorticoids exert powerful modulatory actions on the expression of many pro-inflammatory molecules and they have an important therapeutic role in Graves' disease complicated with TAO. The impact of these steroids on the induction of chemoattractant expression in fibroblasts was determined. Dexamethasone (10 nM) was added to the medium in combination with GD-IgG and fibroblasts were incubated for 16 h. As the data in Table I indicate, the glucocorticoid could block both IL-16 and RANTES induction by Graves' IgG.

EXAMPLE 4

Increased levels of IL-16 IL-16 Dependent T-Cell Migration and RANTES in Serum and Tissues of TAO Patients Referring to FIGS. 3A-3C, serum concentrations of IL-16 are elevated in patients with active TAO. Moreover, both IL-16 and PGHS-2 protein can be detected in TAO orbital tissue. The concentration of IL-16 is determined in sera from either patients with Graves' disease or normal controls. The sera are subjected to an ELISA assay, which utilizes an anti-IL-16 specific antibody. IL-16 is detected by standard immunohistochemical techniques in thin sections harvested from affected orbital connective tissues from a patient with severe Graves' ophthalmopathy. In a separate measurement of IL-16 dependent T-cell migration, a panel of 11 different fibroblast strains from patients with Graves' disease and 5 from individuals without known thyroid disease were challenged with Graves' IgG (100 ng/ml), normal IgG (100 ng/ml) or IL-1β (10 ng/ml) for 24 hours and assessed for T cell migration activity and IL-16 production (Table II). Graves' IgG induced IL-16 dependent cell migration in 10 of the Graves' fibroblast strains which derived from orbit and skin from various anatomic regions. Included were strains from the pretibial skin as well as the abdominal wall and the neck. The latter two sites rarely manifest Graves' disease. A substantial fraction of Graves' IgG provoked T cell migration activity in most of these strains was resistant to neutralization with anti-IL-16. Similarly, chemoattractants produced by RA fibroblasts can be measured by T-cell migration. (data not shown) Fibroblasts are treated with IgG (100 ng/ml) or IL-1β (10 ng/ml) and re-incubated with anti-IL-16 or anti-RANTES antibodies which are shown to partially attenuate chemotasis. RA-IgG in combination with RA synovial fibroblasts produce elevated levels of chemoattractants while similar treatment of non-synovial fibroblasts has no effect.

Referring to Table II below, neutralizing antibodies directed at other chemoattractant molecules demonstrate that the residual activity can be partially attenuated with anti-RANTES Graves' IgG up-regulated both IL-16 and RANTES proteins in eight Graves'-derived fibroblast strains while RANTES was undetectable in two of the Graves' strains exhibiting marked IL-16 inductions. Graves' IgG failed to up-regulate T cell chemotaxis or to induce either IL-16 or RANTES protein in one Graves' strain (orbital strain 9) or in any of the 5 culture strains derived from donors without thyroid disease.

TABLE II

Effects of IgG on IL-16 and RANTES synthesis and T lymphocyte chemotactic production in human fibroblasts.

| Strain | Site | Diagnosis | Treatment | T Cell Migration (% control)$^A$ | +anti-IL-16 | +anti-RANTES | IL-16 (pg/ml)$^B$ | RANTES (pg/ml)$^C$ |
|---|---|---|---|---|---|---|---|---|
| 1 | Orbit | GD | Control | 108 +/− 9 | 102 +/− 4 | 110 +/− 7 | ND | ND |
|  |  |  | Normal IgG | 110 +/− 6 | 104 +/− 7 | 103 +/− 6 | ND | ND |
|  |  |  | GD-IgG | 179 +/− 9 | 142 +/− 8 | 158 +/− 9 | 58 +/− 9 | 83 +/− 10 |
|  |  |  | IL-1β | 194 +/− 11 | 149 +/− 8 | 167 +/− 10 | 71 +/− 9 | 84 +/− 8 |
| 2 | Orbit | GD | Control | 110 +/− 7 | 104 +/− 8 | 107 +/− 9 | ND | ND |
|  |  |  | Normal IgG | 119 +/− 10 | 109 +/− 10 | 116 +/− 11 | ND | ND |
|  |  |  | GD-IgG | 181 +/− 11 | 117 +/− 12 | 171 +/− 9 | 115 +/− 15 | ND |
|  |  |  | IL-1β | 195 ± 13 | 171 ± 7 | 170 ± 8 | 82 ± 9 | 116 ± 11 |
| 3 | Abdominal skin | GD | Control | 108 +/− 10 | 101 +/− 8 | 103 +/− 6 | ND | ND |
|  |  |  | Normal IgG | 110 +/− 11 | 108 +/− 7 | 106 +/− 8 | ND | ND |
|  |  |  | GD-IgG | 187 +/− 10 | 165 +/− 9 | 175 +/− 9 | 90 +/− 9 | 109 +/− 12 |
|  |  |  | IL-1β | 195 +/− 13 | 171 +/− 7 | 171 +/− 8 | 82 +/− 9 | 116 +/− 11 |
| 4 | Orbit | GD | Control | 111 +/− 8 | 105 +/− 6 | 103 ± 4 | ND | ND |
|  |  |  | Normal IgG | 109 +/− 5 | 122 +/− 10 | 113 ± 9 | ND | ND |
|  |  |  | GD-IgG | 280 +/− 12 | 130 +/− 6 | 197 ± 17 | 213 +/− 14 | 98 +/− 9 |
|  |  |  | IL-1β | 236 ± 19 | 175 ± 12 | 188 ± 9 | 194 ± 29 | 128 ± 26 |
| 5 | Abdominal skin | GD | Control | 93 ± 6 | 99 ± 7 | 99 ± 6 | ND | ND |
|  |  |  | Normal IgG | 110 ± 9 | 107 ± 8 | 104 ± 8 | ND | ND |
|  |  |  | GD-IgG | 157 ± 6 | 132 ± 8 | 142 ± 9 | ND | ND |
|  |  |  | IL-1β | 144 ± 8 | 128 ± 8 | 131 ± 5 | ND | ND |
| 6 | Neck skin | GD | Control | 103 ± 5 | 100 ± 7 | 104 ± 6 | ND | ND |
|  |  |  | GD-IgG | 195 ± 11 | 153 ± 12 | 168 ± 8 | 97 ± 21 | 198 ± 30 |
|  |  |  | IL-1β | 211 ± 13 | 148 ± 10 | 178 ± 12 | 116 ± 27 | 253 ± 42 |
| 7 | Pretibial skin | GD | Control | 112 ± 9 | 109 ± 7 | 104 ± 8 | ND | ND |
|  |  |  | Normal IgG | 108 ± 7 | 101 ± 6 | 103 ± 9 | ND | ND |
|  |  |  | GD-IgG | 213 ± 11 | 168 ± 9 | 179 ± 10 | 168 ± 23 | 119 ± 17 |
|  |  |  | IL-1β | 236 ± 19 | 175 ± 12 | 188 ± 9 | 194 ± 29 | 128 ± 26 |
| 8 | Pretibial skin | GD | Control | 109 ± 8 | 107 ± 8 | 111 ± 9 | ND | ND |
|  |  |  | Normal IgG | 114 ± 9 | 112 ± 5 | 114 ± 10 | ND | ND |
|  |  |  | GD-IgG | 167 ± 9 | 126 ± 8 | 150 ± 6 | 58 ± 24 | ND |
|  |  |  | IL-1β | 204 ± 14 | 164 ± 10 | 173 ± 8 | 79 ± 11 | ND |
| 9 | Orbit | GD | Control | 109 ± 7 | 104 ± 8 | 104 ± 9 | ND | ND |
|  |  |  | Normal IgG | 106 ± 8 | 101 ± 6 | 109 ± 9 | ND | ND |
|  |  |  | GD-IgG | 111 ± 5 | 106 ± 8 | 104 ± 10 | ND | ND |
|  |  |  | IL-1β | 243 +/− 13 | 167 +/− 11 | 189 +/− 10 | 218 +/− 33 | 78 +/− 21 |

TABLE II-continued

Effects of IgG on IL-16 and RANTES synthesis and T lymphocyte chemotactic production in human fibroblasts.

| Strain | Site | Diagnosis | Treatment | T Cell Migration (% control)[A] | +anti-IL-16 | +anti-RANTES | IL-16 (pg/ml)[B] | RANTES (pg/ml)[C] |
|---|---|---|---|---|---|---|---|---|
| 10 | Orbit | GD | Control | 105 +/− 8 | 109 +/− 10 | 104 +/− 5 | ND | ND |
|  |  |  | Normal IgG | 101 +/− 9 | 100 +/− 7 | 108 +/− 8 | ND | ND |
|  |  |  | GD-IgG | 221 +/− 13 | 172 +/− 8 | 189 +/− 11 | 159 +/− 28 | 195 +/− 35 |
|  |  |  | IL-1β | 248 +/− 19 | 189 +/− 14 | 206 +/− 12 | 246 +/− 32 | 214 +/− 30 |
| 11 | Orbit | GD | Control | 106 +/− 7 | 104 +/− 8 | 101 +/− 5 | ND | ND |
|  |  |  | Normal IgG | 110 +/− 10 | 107 +/− 5 | 103 +/− 7 | ND | ND |
|  |  |  | GD-IgG | 195 +/− 11 | 135 +/− 9 | 159 +/− 7 | 47 +/− 7 | 26 +/− 8 |
|  |  |  | IL-1β | 210 +/− 13 | 162 +/− 11 | 183 +/− 6 | 94 +/− 12 | 69 +/− 6 |
| 12 | Orbit | Normal | Control | 108 +/− 9 | 109 +/− 4 | 101 +/− 7 | ND | ND |
|  |  |  | GD-IgG | 110 +/− 9 | 105 +/− 8 | 112 +/− 8 | ND | ND |
|  |  |  | Normal IgG | 104 +/− 6 | 109 +/− 5 | 107 +/− 6 | ND | ND |
|  |  |  | IL-1β | 168 +/− 11 | 143 +/− 9 | 156 +/− 9 | 56 +/− 10 | 42 +/− 9 |
| 13 | Orbit | Normal | Control | 92 +/− 4 | 90 +/− 7 | 94 ± 6 | ND | ND |
|  |  |  | GD-IgG | 106 +/− 9 | 95 +/− 5 | 99 ± 8 | ND | 10 +/− 8 |
|  |  |  | Normal IgG | 92 +/− 9 | 97 +/− 6 | 101 ± 5 | ND | ND |
| 14 | Orbit | Normal | Control | 102 +/− 8 | 104 +/− 5 | 105 +/− 7 | ND | ND |
|  |  |  | GD-IgG | 108 +/− 5 | 108 +/− 4 | 103 +/− 9 | ND | ND |
|  |  |  | Normal IgG | 109 +/− 8 | 104 +/− 7 | 106 +/− 5 | ND | ND |
|  |  |  | IL-1β | 189 +/− 10 | 154 +/− 9 | 159 +/− 9 | 68 +/− 9 | 79 +/− 11 |
| 15 | Extremity Skin | Normal | Control | 103 ± 4 | 103 ± 8 | 100 ± 6 | ND | ND |
|  |  |  | GD-IgG | 106 ± 9 | 104 ± 7 | 103 ± 8 | ND | ND |
|  |  |  | Normal IgG | 105 ± 7 | 107 ± 7 | 101 ± 5 | ND | ND |
|  |  |  | IL-1β | 197 ± 10 | 153 ± 9 | 172 ± 9 | 138 ± 15 | 173 ± 12 |
| 16 | Extremity Skin | Normal | Control | 108 ± 8 | 103 ± 7 | 105 ± 10 | ND | ND |
|  |  |  | Normal IgG | 107 ± 6 | 104 ± 8 | 103 ± 6 | ND | ND |
|  |  |  | GD-IgG | 100 ± 6 | 106 ± 7 | 101 ± 5 | ND | ND |
|  |  |  | IL-1β | 201 ± 7 | 155 ± 8 | 173 ± 7 | 98 ± 19 | 125 ± 9 |

[A]Lymphocyte chemotaxis assay of medium from fibroblasts treated with IL-1β (10 ng/ml), Graves' disease IgG (100 ng/ml) or IgG (100 ng/ml) from donors without known thyroid disease. Chemotactic activity is expressed as a percent of control, the activity levels of which were found in fibroblast cultures not treated with IL-1β or IgG. IL-16 and RANTES-dependent activity is defined as the difference in chemotaxis observed in samples without and with the respective neutralizing Abs. Data are expressed as the mean ± S.D. of three independent determinations. Migration greater than 35% was significant at 5% confidence limit
[B]Limits of detection 20 pg/ml
[C]Limits of detection 15 pg/ml

EXAMPLE 5

Orbital Fibroblasts Display Functional CD40 and Express Extremely High Levels of CD154

Figure 6A:
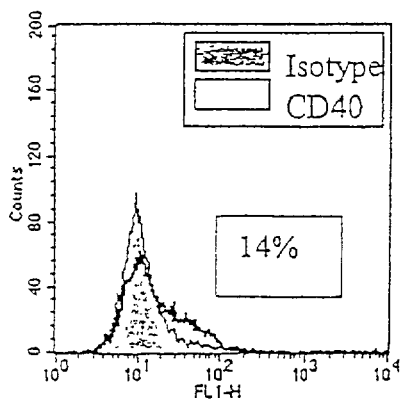
FIGS. 6A, 6B, and 6C show the bimodal expression of CD40 in orbital fibroblasts.
Figure 6B:
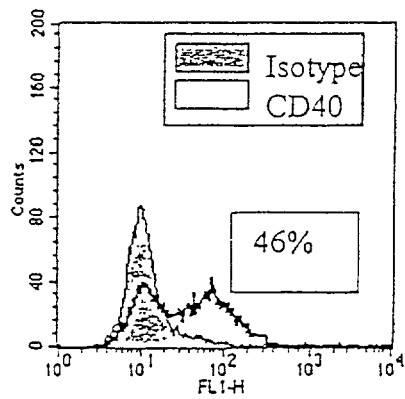
Figure 6C:
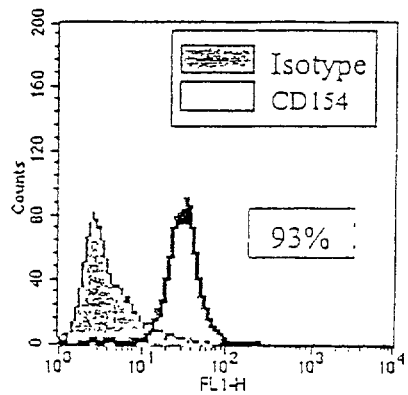

Orbital fibroblasts express and display relatively high levels of CD40 mRNA and protein, even under basal culture conditions. This is unusual in that the other fibroblasts where CD40 has thus far been detected (lung, gingiva, synovium) all require interferon γ priming before CD40 becomes easily detected. When treated with interferon γ or serum, the levels of CD40 are enhanced substantially. Referring to FIGS. 6A-6C, the CD40 expression in orbital fibroblasts is bimodal. When analyzed with flow cytometry, approximately 50% of Thy-1+ and Thy-1− fibroblasts display CD40. This finding suggests that a sub-population of these fibroblasts directly interacts with lymphocytes through the CD40/CD154 conduit, while those not expressing CD40 receive signals through other cytokine receptors. In addition to CD40, the unanticipated expression of extremely high levels of CD154 in TAO fibroblasts (FIG. 6C) implicates the CD40/CD 154 conduit in fibroblast auto-activation.

The CD40 displayed on orbital fibroblasts, when ligated with recombinant CD154, is competent to signal a number of downstream genes that appear relevant to the pathogenesis of TAO. These include IL-6 and IL-8, two important molecules critical to the activation and trafficking of bone marrow derived cells to sites of inflammation and which have been implicated in Graves' disease. When orbital fibroblasts are treated with rCD154, the synthesis of both IL-6 and IL-8 is dramatically increased. Nuclear translocation of NF-κB is provoked by CD40 ligation and inhibiting the activation of this transcriptional factor by stabilizing the NF-κB/IκB complex can block the induction of both IL-6 and IL-8.

EXAMPLE 6

Figure 7A:
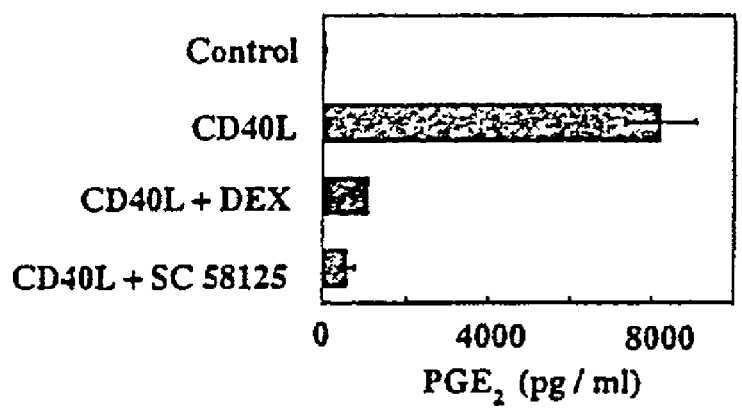
FIGS. 7A and 7B show the up-regulation of $PGE_2$ synthesis and blockage with SC58125 (a PGHS-2 inhibitor) and dexamethasone (7A) and PGHS-2 expression (7B) in TAO fibroblasts.
Figure 7B:
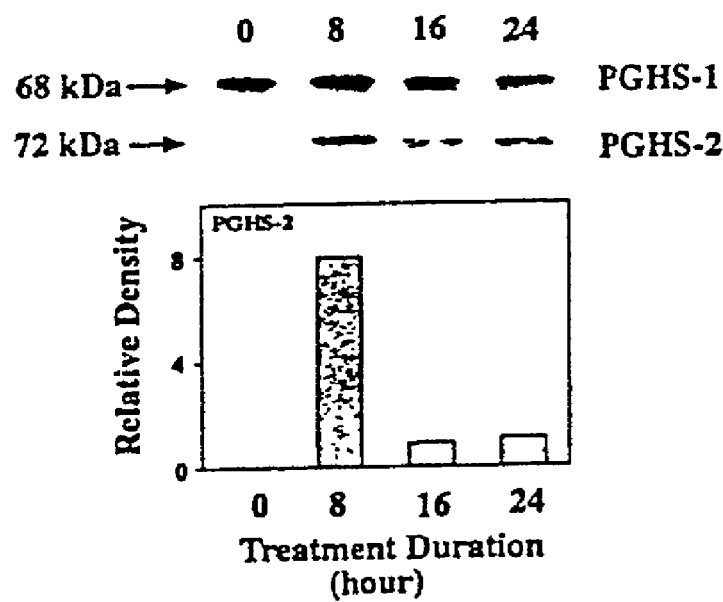

Activation of the CD40/CD154 Bridge Mediates the Up-Regulation Of PGHS-2 and PGE$_2$ Synthesis Referring to FIGS. 7A and 7B, CD40 ligation in orbital fibroblasts results in the induction of PGHS-2 and leads to the over-production of PGE$_2$. The magnitude of these inductions is known to be comparable to that observed following treatment with IL-1β and leukoregulin. CD40 ligation in these cultures results in the intermediate activation of IL-1α gene expression. This induction occurs after 6 h of treatment and is mediated at the pre-translational level. IL-1β is undetectable in orbital fibroblasts and is not induced by CD154. Interrupting the expression, receptor binding or activity of IL-1α attenuates the induction of PGHS-2 provoked by CD40 ligation. It is notable that CD40 is over-expressed by thyroid epithelium in Graves' disease and provokes constitutive PGHS-2 expression. Moreover, functional CD40 is expressed by human thyroid fibroblasts.

EXAMPLE 7

Figure 8A:
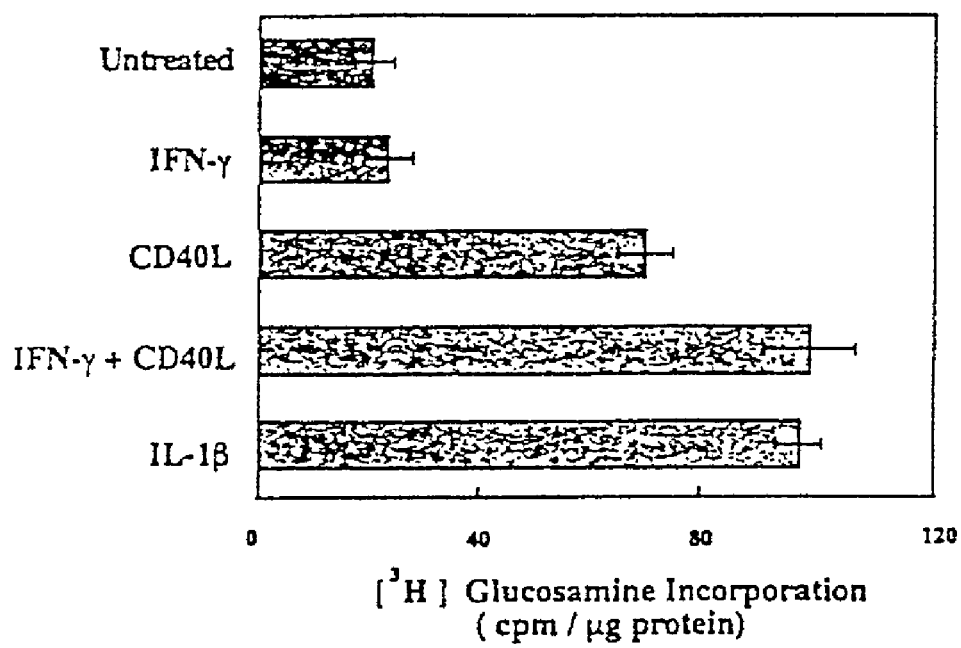
FIGS. 8A and 8B are CD40/CD154 induced hyaluronan (8A) and collagen I (8B) synthesis in orbital fibroblasts.
Figure 8B:
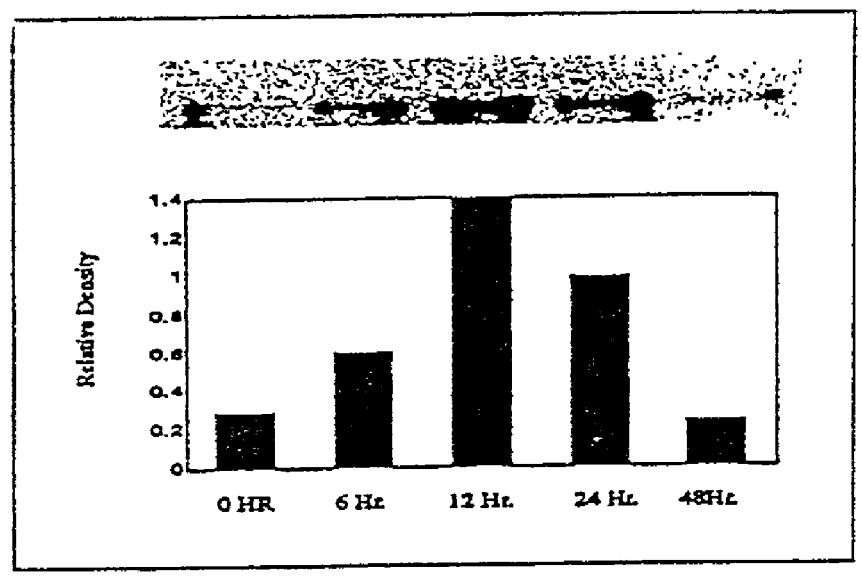

CD40/CD154 Bridge Activation in Orbital Fibroblasts Results in Substantial Increases in Hyaluronan and Collagen Another consequence of CD40 ligation is the up-regulation of hyaluronan synthesis, consistently 4-5-fold above controls (See FIG. 8A). These effects are specific and the consequence of a very modest increase in HAS2 but a robust induction of UDP-glucose dehydrogenase. This NAD$^+$-linked oxidoreductase enzyme, immediately up-stream from the HAS enzymes, catalyzes the conversion of UDP-glucose to UDP-glucuronate. UDP-glucuronate in turn provides the D-glucuronate of hyaluronan, chondroitin sulfate and heparan sulfate. These fibroblasts synthesize multiple large and small heparan sulfates as well as chondroitin and dermatan sulfates. In concert with the increased hyaluronan synthesis is the up-regulation of collagen in fibroblasts. As FIG. 8B indicates, the induction of type I collagen is time-dependent and of substantial magnitude (3-4 fold). CD40 ligation in TAO fibroblasts also leads to the up-regulation of matrix metalloproteinases and the degradation of the anti-fibrotic proteoglycan, decorin and biglycan not shown which is not elicited by IL-1β. The significance of the degradation of these proteoglycans relates, in part, to their function as "sinks" for cytokines and important chemoattractants. Moreover, the extracellular matrix functions as an important barrier for partitioning the cellular microenvironment. The disordered economy of extra-cellular matrix, especially hyaluronan, is a cardinal feature of the tissue remodeling associated with TAO.

Figure 9A:
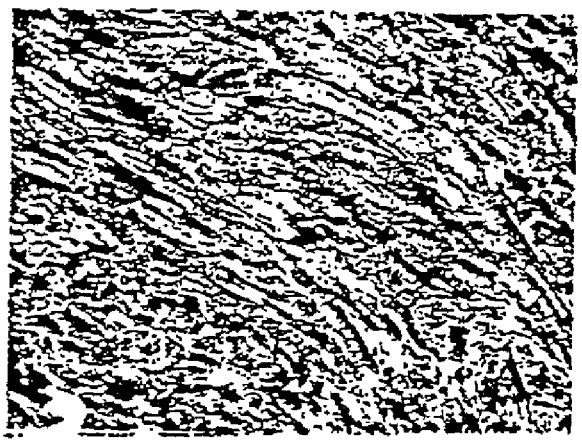
FIGS. 9A and 9B are thin sections of orbital connective tissue and smooth muscle stained with anti-CD40.
Figure 9B:
Figure 10A:
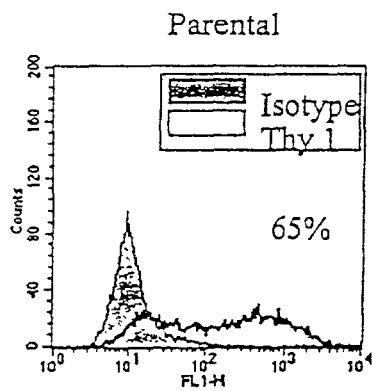
FIGS. 10A-10C are fibroblasts from the orbital connective tissue depot divided by parental (10A), Thy-1+ (10B), and Thy-1− (10C) phenotypic subsets.
Figure 10B:
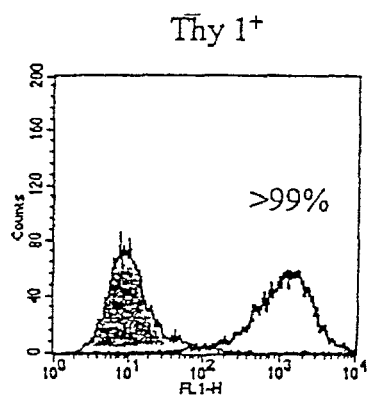
Figure 10C:
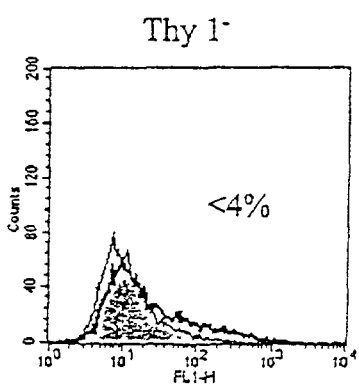

Referring to FIGS. 9A-9B, the clear up-regulation of CD40 expression in connective tissue in situ from the TAO orbit shows that the expression of CD154, display of CD40 on orbital fibroblasts, and signaling initiated through ligation, represent key aspects underlying the tissue remodeling provoked by T cells in TAO. This data also indicates the same mechanism in inflammatory mechanisms underlying disease-specific, IgG-mediated, inflammation in RA.

EXAMPLE 8

Orbital Fibroblasts can be Divided into Phonotype Subsets on the Basis of Thy-1 Expression As noted above, orbital fibroblasts, specifically those derived from the connective/adipose tissue depot, are heterogenous with regard to the display of the surface marker Thy-1. Several different strains of fibroblasts have been developed that are either homogenously positive or negative for Thy-1 expression and which are stable with regard to expression of Thy-1 over many population doublings and serial passages. Orbital fibroblasts represent the first human fibroblast type shown to be heterogeneous with respect to Thy-1 expression. For instance, dermal fibroblasts from all anatomic regions thus far examined, uniformly express Thy-1, however segregating orbital fibroblasts on the basis of Thy-1 expression has yielded distinct sub-groups of cells that exhibit different phenotypes. Fibroblasts from the endomesium of extra-ocular muscles are homogenous in that they uniformly display Thy-1 and are expected to behave like Thy-1$^+$ fibroblasts derived from the connective tissue of the orbit.

Figure 11A:
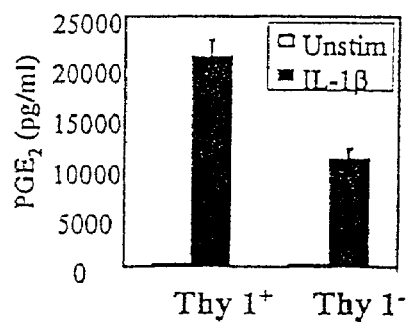
FIGS. 11A-11C show differential production in TAO-derived Thy-1+ and Thy-1− subsets of $PGE_2$ (11A) and IL-8 in response to IL-1β stimulation (11B), and IL-16 in response to stimulation with Graves' IgG (11C).
Figure 11B:
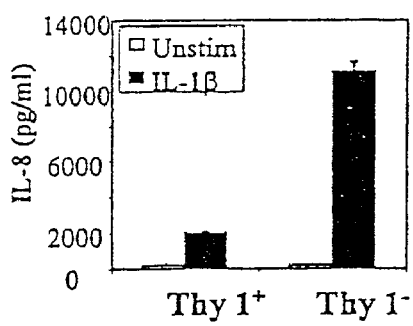
Figure 11C:
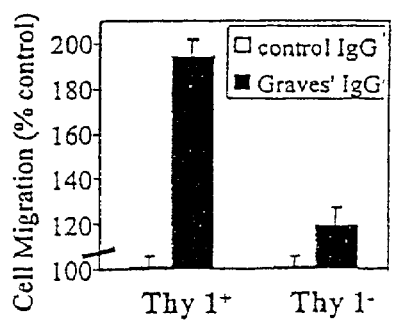
Figure 12A:
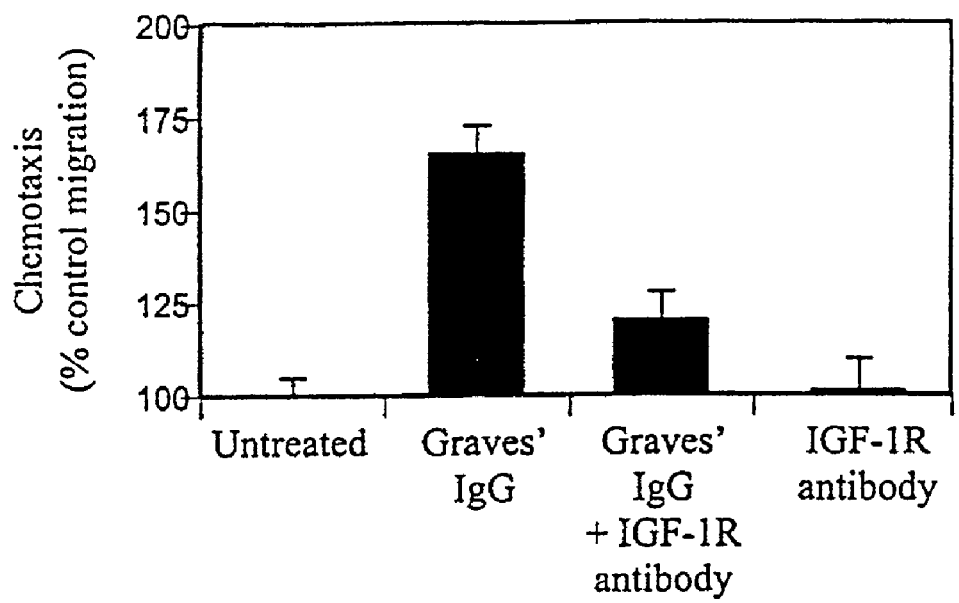
FIGS. 12A and 12B show the IGF-receptor mediation of Graves' disease specific IgG.
Figure 12B:
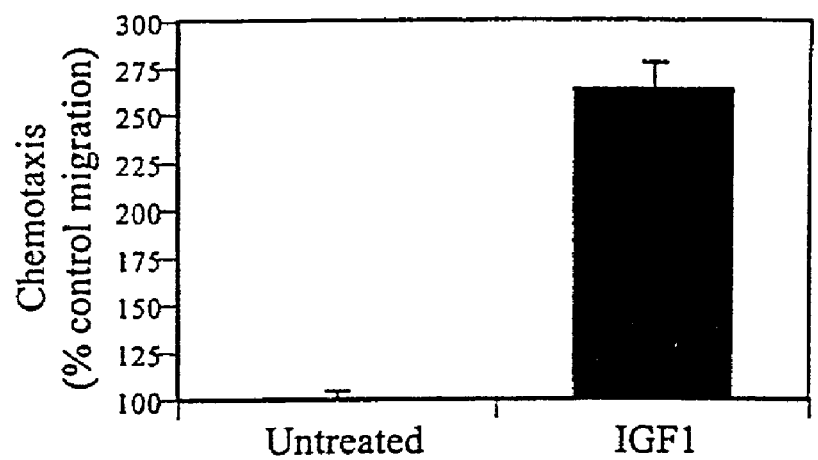
Figure 13A:
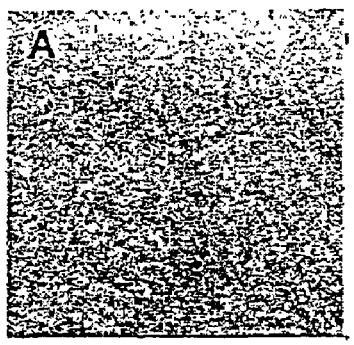
FIGS. 13A-13D show induction of differentiation of Thy-1− orbital fibroblasts into adipocytes by the PPARα ligand rosiglitazone. A control phase contrast of parental strain (B) flow cytometric analysis of parental strain showing absence of adipocytes (C) phase contrast post-differentiation showing adipocyte clusters (D) flow analysis showing 44% adipocyte differentiated.
Figure 13B:
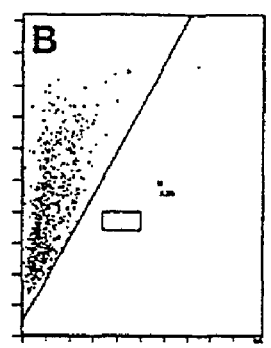
Figure 13C:
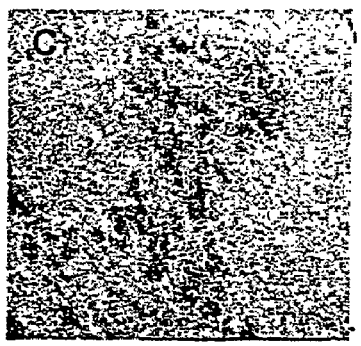
Figure 13D:
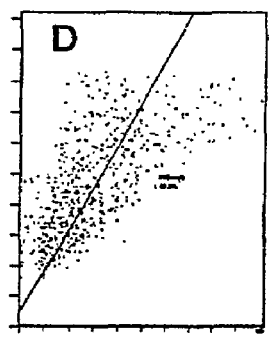
Figure 14:
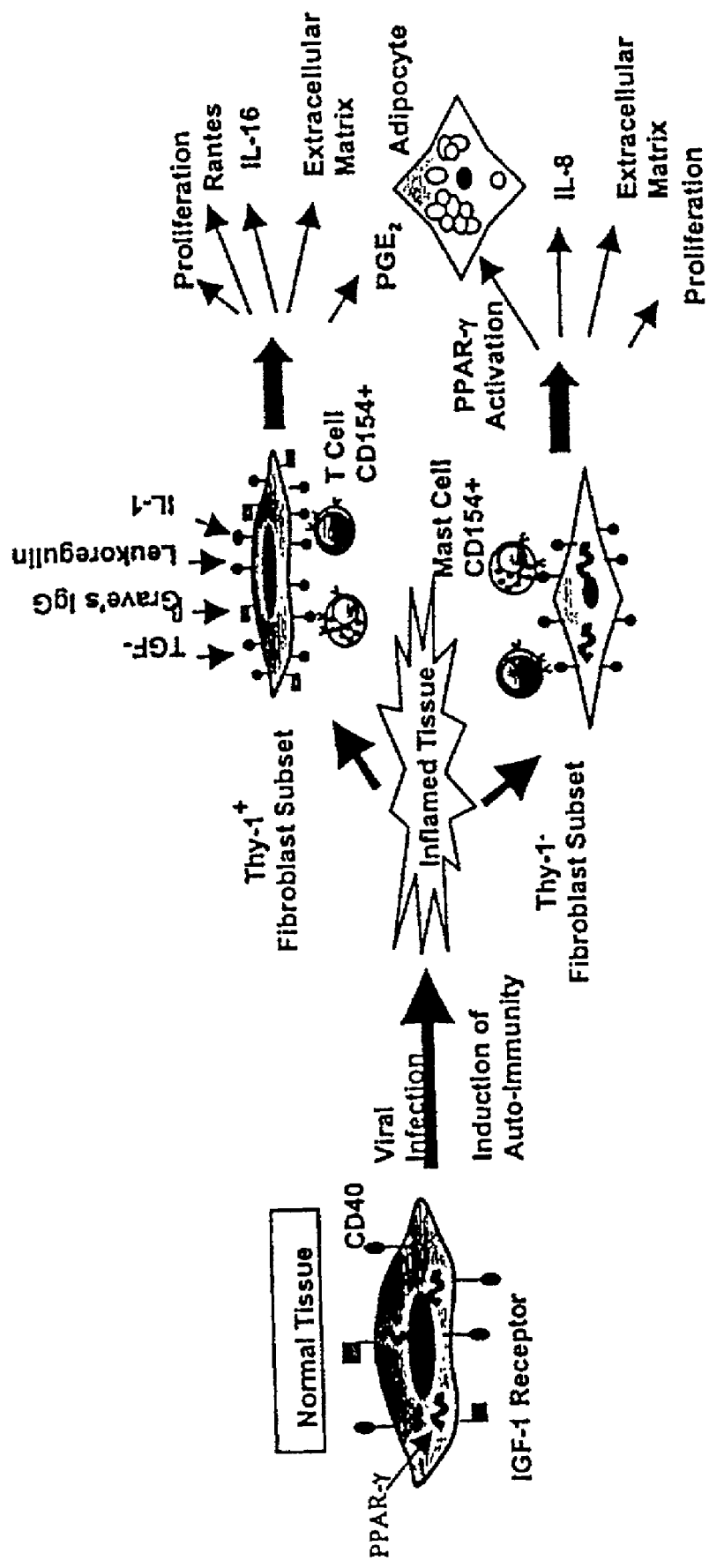
FIG. 14 is a model of the role of CD40 and Thy-1 phenotypic subset fibroblasts in TAO pathogenesis.

Referring to FIGS. 11A-11C, phenotype subsets of fibroblasts exhibit different phenotypes in culture. Both express constitutive PGHS-1 and when treated with IL-1β, express high levels of PGHS-2 and produce large amounts of PGE$_2$. Thy-1$^+$ subsets consistently produce more PGE$_2$ than do Thy-1$^-$ fibroblasts (FIG. 11A). Both subsets contain cells that display Class I MHC molecules under unprovoked conditions. In contrast, neither subset expressed Class II MHC DR under basal culture conditions. When treated with interferon γ (100 U/ml), cells from both subsets express and display HAL-DR. The levels of expression are considerably higher in Thy-1$^-$ cells and the induction can be attenuated with glucocorticoids. DR expression is considerably higher in fibroblasts from TAO connective tissue compared with those from normal tissue. These findings implicate the Thy-1$^-$ subset as the cell type possessing exaggerated foreign antigen presenting activity and therefore a greater potential for activating macrophages and lymphocytes.

With regard to cytokine expression, both subsets fail to generate detectable IL-6 under basal culture conditions but synthesize high levels of the cytokine when treated with IL-1β. The magnitude of these responses is similar in the two fibroblast populations. Similarly, both subsets express low basal levels of IL-8 (FIG. 11B). When treated with IL-1β, Thy-1$^-$ fibroblasts synthesize and release extremely high levels of IL-8 and this induction is substantially (5.5-fold) greater than that occurring in the Thy-1$^+$ subset. This finding suggests a divergence between Thy-1$^+$ and Thy-1$^-$ fibroblasts with regard to their potential to signal specific bone-marrow derived cells and participate in the trafficking of those cells to the orbit.

EXAMPLE 9

Thy-1$^+$ Orbital Fibroblasts Interact with Graves' Disease Specific IgG Leading to an Induction of IL-16 and RANTES Through the IGF-1 Receptor The well-characterized and widely-appreciated presence of antibodies of the IgG1 subclass that bind to the TSHr and mimic authentic TSH has been considered to represent the sole pathogenic immunoglobulin in the disease. Moreover, the TSHr displayed on fibroblasts is widely believed to represent the target to which Graves' disease-specific antibodies bind and TSHr is expressed in cells of the fibroblast/preadipocyte lineage from a wide array of depots. However, treatment of these cells with high concentrations of TSH fails to provoke the expression of IL-16 or RANTES, suggesting that TSHr is not involved. Moreover, competing the IgG with high concentrations of asialo HCG, a TSHr antagonist, fails to attenuate the induction of either IL-16 or RANTES thereby suggesting that another surface receptor mediates the orbital fibroblasts response to IgG.

Referring to FIGS. 11A and 11B, employing an extremely specific IGF-1 receptor antagonist antibody (αIR3, 5 µg/ml, Collaborative Research), the induction of IL-16 and RANTES by IgG in TAO orbital fibroblasts is blocked (FIG. 11A) while induction is mimicked. Thus, with authentic IGF-1 (10 nM), the IGF-1 receptor mediates the effects of Graves' disease-specific IgG on IL-16 and RANTES expression in TAO orbital fibroblasts and demonstrates that the IgG relevant to TAO is not directed against an epitope of TSHr but instead, toward the IGF-1 receptor.

In another set of experiments designed to examine the phenotype of extra-ocular muscle-derived fibroblasts, these cells are shown to differ from those derived from the connective/adipose tissue of the orbit. This dichotomy could have been anticipated from the clinical presentation of some patients with TAO who present with disease confined to either the extra-ocular muscle perimesium or to the posterior compartment (connective tissue). The former is seen more commonly in elderly patients while the latter more frequently in children. Perimesial fibroblasts uniformly display Thy-1 and possess the phenotypic attributes associated with Thy-1$^+$ cells in the connective tissue compartment, including the expression of IL-16 and particularly robust inductions of PGE$_2$ synthesis. On the other hand, perimesial fibroblasts are refractory to the induction of adipogenic differentiation utilized successfully to induce this differentiation in Thy-1⁻ connective tissue fibroblasts. Thus, these cells can now be insinuated directly in the active processes of lymphocyte recruitment and fibrosis, two aspects of TAO known to involve the connective tissue investments of the extra-ocular muscles.

EXAMPLE 10

Thy-1⁻ Orbital Fibroblasts are Pre-Adipocytes Capable of Terminal Differentiation In Vitro An under-appreciated feature of the tissue remodeling associated with TAO is the expansion of the fat deposit. In fact, a number of surgical therapeutic strategies are aimed directly at reducing the mass of fat in TAO. These have been variably successful in reducing the mechanical embarrassment imposed by excessive fat volumes in TAO. Orbital fibroblasts from the connective/adipose tissue depot possess the potential to undergo in vitro differentiation into mature adipocytes and in so doing to augment the mass of that tissue in the contact of TAO. While only a small fraction of orbital fibroblasts undergo differentiation into mature adipocytes, the fraction is invariant with regard to whether the fibroblasts were from a patient with TAO or from normal orbital tissues. While this discovery was of substantial interest to us, we realized that the differentiation of such a small fraction of cells might preclude determining the phenotypic changes accompanying them. However, referring to FIGS. 12A-12D, transient exposure to the PPARγ ligand (rosiglitazone) 45 to 65% of the cells in a parent strain matured to adipocytes showing that orbital fibroblasts express abundant PPARγ. Moreover, the preadipocytes are uniformly Thy-1⁻, and Thy-1⁺ cells do not differentiate into mature adipocytes. As noted above, unlike fibroblasts from the adipose/connective tissue depot, those from the perimesium uniformly fail to differentiate under the same conditions. Therefore, a set of factors is defined which drive the adipogenic differentiation of orbital connective/adipose tissue.

All publications mentioned in this specification are herein incorporated by reference to the same extent as if each individual publication was specifically and individually indicated to be incorporated by reference.

We claim:

1. A method of detecting Graves' disease in a patient comprising
   (a) obtaining an orbital or skin sample comprising fibroblasts from the patient,
   (b) contacting said fibroblasts with disease specific IgG from the same patient, and
   (c) detecting in said an orbital or skin sample binding of disease specific IgG to the IGF-1 receptor (IGF-1R) relative to a control wherein said binding of disease specific IgG to the IGF-1 receptor (IGF-1R) activates fibroblasts, wherein an increased presence of IgG-activated fibroblasts compared to the control indicates Graves' disease, and wherein fibroblast activation is determined by measuring the level of IL-16 expressed by said IgG-activated fibroblasts, RANTES expressed by said IgG-activated fibroblasts or by measuring T cell migration towards said fibroblasts in said orbital or skin sample.

2. The method of claim 1, wherein an elevated level of said IL-16 compared to the control indicates presence of said IgG-activated fibroblasts.

3. The method of claim 1, wherein the detecting is accomplished by exposing T-cells to said orbital or skin sample comprising said fibroblasts and measuring T-cell migration toward said fibroblasts, wherein an increase in the migration of said fibroblasts relative to the control indicates presence of said IgG-activated fibroblasts.

4. The method of claim 1, wherein the patient is human.

5. The method of claim 1, wherein an elevated level of said RANTES compared to the control indicates presence of said IgG-activated fibroblasts.

6. The method of claim 1, wherein said increased T cell migration compared to the control indicates presence of said IgG-activated fibroblasts.

\* \* \* \* \*